(12) United States Patent
Brandt et al.

(10) Patent No.: US 12,163,939 B2
(45) Date of Patent: Dec. 10, 2024

(54) GAS LEAK DETECTION SYSTEM

(71) Applicant: Earthview Corporation, Longmont, CO (US)

(72) Inventors: Duncan Brandt, Longmont, CO (US); Jim Maslanik, Lafayette, CO (US); Frederick Givhan, Longmont, CO (US)

(73) Assignee: Earthview Corporation, Longmont, CO (US)

(*) Notice: Subject to any disclaimer, the term of this patent is extended or adjusted under 35 U.S.C. 154(b) by 123 days.

(21) Appl. No.: 17/735,436

(22) Filed: May 3, 2022

(65) Prior Publication Data
US 2022/0357232 A1 Nov. 10, 2022

Related U.S. Application Data

(60) Provisional application No. 63/292,805, filed on Dec. 22, 2021, provisional application No. 63/292,763, (Continued)

(51) Int. Cl.
G01N 33/00 (2006.01)
G01M 3/04 (2006.01)
(Continued)

(52) U.S. Cl.
CPC .......... *G01N 33/0034* (2013.01); *G01M 3/04* (2013.01); *G01N 33/0075* (2013.01); *G01M 3/16* (2013.01); *G01M 3/18* (2013.01)

(58) Field of Classification Search
CPC .......... G01N 33/0034; G01N 33/0036; G01N 33/0075; G01M 3/04; G01M 3/16; G01M 3/007
See application file for complete search history.

(56) References Cited

U.S. PATENT DOCUMENTS 10,031,040 B1 7/2018 Smith
10,168,276 B1 * 1/2019 Stambaugh ........ G01N 33/0047
(Continued)

OTHER PUBLICATIONS

Wolfrum et al., "Metal oxide sensor arrays for the detection, differentiation, and quantification of volatile organic compounds at sub-parts-per-million concentration levels", Sensors and Actuators B, vol. 115, Nov. 2, 2005, pp. 322-329.
(Continued)

*Primary Examiner* — Nathaniel J Kolb
(74) *Attorney, Agent, or Firm* — Blank Rome LLP

(57) ABSTRACT

A gas leak detection system that combines sensor units having an array of sensors that detect natural gas and the volatile organic compounds and variable atmospheric conditions that confound existing gas leak detection methods, a specially designed sensor housing that limits the variability of those atmospheric conditions, and a machine learning-enabled process that uses the wide array of sensor data to differentiate between natural gas leaks and other confounding factors. Multiple low-cost sensor units can be used to monitor gas concentrations at multiple locations across a site (e.g., a well pad or other oil or natural gas facility), enabling the gas leak detection system to model gas leak emission rates in two- or three-dimensional space to reveal the most likely origin of the gas leak.

20 Claims, 23 Drawing Sheets

Related U.S. Application Data filed on Dec. 22, 2021, provisional application No. 63/184,669, filed on May 5, 2021.

(51) Int. Cl.
    *G01N 3/16*     (2006.01)
    *G01M 3/16*     (2006.01)
    *G01M 3/18*     (2006.01)

(56) References Cited

U.S. PATENT DOCUMENTS

| | | | |
|---|---|---|---|
| 10,386,258 | B1 | 8/2019 | Steele |
| 10,948,471 | B1* | 3/2021 | MacMullin ........ G01N 33/0047 |
| 10,962,437 | B1 | 3/2021 | Nottrott |
| 2004/0215402 | A1* | 10/2004 | Hsiung .............. G01N 33/0031 |
| | | | 702/22 |
| 2014/0032129 | A1 | 1/2014 | Rella |
| 2017/0026722 | A1 | 1/2017 | Schwartz et al. |
| 2018/0156766 | A1* | 6/2018 | Zeng .................... G01N 33/004 |
| 2018/0225426 | A1 | 8/2018 | Murthy |
| 2018/0321208 | A1 | 11/2018 | Bai |
| 2019/0285504 | A1 | 9/2019 | Muralidhar |
| 2020/0019168 | A1* | 1/2020 | Guzman .............. G01N 33/004 |
| 2020/0232959 | A1* | 7/2020 | Armitage ................ E21B 41/00 |
| 2020/0333307 | A1* | 10/2020 | Armitage ................ G08B 21/16 |
| 2021/0102925 | A1* | 4/2021 | Gogoana .............. G01N 33/007 |
| 2021/0109049 | A1* | 4/2021 | Potyrailo ............. G01N 27/026 |
| 2022/0366108 | A1 | 11/2022 | Filippov |

OTHER PUBLICATIONS

Bicelli et al., "Model and Experimental Characterization of the Dynamic Behavior of Low-Power Carbon Monoxide MOX Sensors Operated with Pulsed Temperature Profiles", IEEE Transactions on Instrumentation and Measurements. vol. 58, No. 5, May 2009, pp. 1324-1332.

Zhu et al., "An ultra-low power switch array of temperature and humidity sensors with direct digital output", Transducers, Jun. 16, 2013, pp. 108-111.

International Search Report and Written Opinion; International Application No. PCT/US2022/027487; International Filing Date: May 3, 2022; 29 pages.

Hirst et al., Locating and quantifying gas emission sources using remotely obtained concentration data, Atmospheric Environment 74, 2013, pp. 141-158, www.elsevier.com/locate/atmosenv.

Bennetts et al., Creating true gas concentration maps in presence of multiple heterogeneous gas sources, IEEE Sensors, 2012.

Allen et al., Improving pollutant source characterization by better estimating wind direction with a genetic algorithm, Atmospheric Environment 41, 2007, pp. 2283-2289, www.elsevier.com/locate/atmosenv.

Bennetts et al., Robot Assisted Gas Tomography—Localizing Methane Leaks in Outdoor Environments, IEEE ICRA, 2014, pp. 6362-6367.

Haupt et al., Validation of a Receptor-Dispersion Model Coupled with Genetic Algorithm Using Synthetic Data, American Meteorological Society, vol. 45, 2006, pp. 476-490.

Long et al., Assessing sensitivity of source term estimation, Atmospheric Environment 44, 2010, pp. 1558-1567, www.elsevier.com/locate/atmosenv.

* cited by examiner

GAS LEAK DETECTION SYSTEM

CROSS-REFERENCE TO RELATED APPLICATIONS

This application claims priority to U.S. Prov. Pat. Appl. No. 63/184,669, filed May 5, 2021, U.S. Prov. Pat. Appl. No. 63/292,805, filed Dec. 22, 2021, and U.S. Prov. Pat. Appl. No. 63/292,763, filed Dec. 22, 2021, which are hereby incorporated by reference.

FEDERAL FUNDING

None

BACKGROUND

Reducing air pollution and greenhouse gasses are critically important steps toward slowing the rate of climate change and improving overall air quality. Therefore, detecting natural gas leaks and identifying the origin of those natural gas leaks are important tasks, particularly at well pads and other oil or natural gas facilities.

Inexpensive metal oxide gas sensors are quite sensitive to natural gases such as methane and ethane, but that sensitivity is swamped by their sensitivity to volatile organic compounds that may be present in the atmosphere, variations in the atmospheric moisture content and temperature, and even the temperature of the sensor housing itself. Additionally, while metal oxide sensors have a relatively long life span compared to other types of sensors like photoionization detectors (PIDs) and chemically reactive sensors, metal oxide sensors are subject to degradation and/or a change in sensor response over time. Therefore, prior art natural gas detection methods have been unable to utilize inexpensive metal oxide gas sensors in a way that accurately differentiates between sensor responses to natural gas leaks and sensor responses to other, unrelated conditions.

Instead, existing methods include collecting air samples to be analyzed at a lab or using science-grade instruments, high-precision handheld gas measurement instruments, or optical gas imaging (OGI) cameras. In each instance, the high cost of the equipment and the need for human operators prevents those methods from being used to continuously monitor an array of locations across the site of a potential gas leak. Furthermore, because the number of the air sampling locations is limited, existing methods do not provide a sufficient number of observations to identify the origin of a gas leak or estimate the rate of a gas leak. Finally, those expensive and time intensive methods are poorly suited for citizen-driven monitoring (e.g., in neighborhoods that may be near buried, leaking pipelines or active drilling sites) that can help detect and pinpoint locations of potential leaks before they reach dangerous, explosive levels.

Accordingly, there is a need for a system that uses inexpensive metal oxide sensors to detect gas leaks from a number of locations and models the emissions and dispersion of those gas leaks to reveal the likely origin of those gas leaks. To do so, there is a need for a system that differentiates between the response of metal oxide gas sensors to natural gas and the response of those sensors to unrelated conditions, including other volatile organic compounds in the atmosphere, variations in the atmospheric moisture content and temperature, and the temperature of the sensor housing itself.

SUMMARY

Disclosed is a gas leak detection system that combines sensor units having an array of sensors that detect natural gas and the volatile organic compounds and variable atmospheric conditions that confound existing gas leak detection methods, a specially designed sensor housing that limits the variability of those atmospheric conditions, and a machine learning-enabled process that uses the wide array of sensor data to differentiate between natural gas leaks and other confounding factors.

To differentiate between natural gas and volatile organic compounds, the machine learning-enabled process takes advantage of the varying responsiveness of each sensor in the array to measure the concentrations of both natural gas and volatile organic compounds. The machine learning-enabled process can also easily incorporate additional data from additional sensors (e.g., additional gas sensors, directional microphones, etc.) to detect other gases, to more accurately detect natural gas leaks, etc.

The sensor units can autonomously and continuously monitor potential gas sources, even in remote locations without access to power, and select the best available communication network to maintain communication with a remote monitoring system. Because the sensor units are low cost, multiple sensor units can be used to monitor gas concentrations at multiple locations across a site (e.g., a well pad or other oil or natural gas facility), enabling the gas leak detection system to model gas leak emission rates in two- or three-dimensional space to reveal the most likely origin of the gas leak.

BRIEF DESCRIPTION OF THE DRAWINGS

Aspects of exemplary embodiments may be better understood with reference to the accompanying drawings. The components in the drawings are not necessarily to scale, emphasis instead being placed upon illustrating the principles of exemplary embodiments.

DETAILED DESCRIPTION

Figure 1:
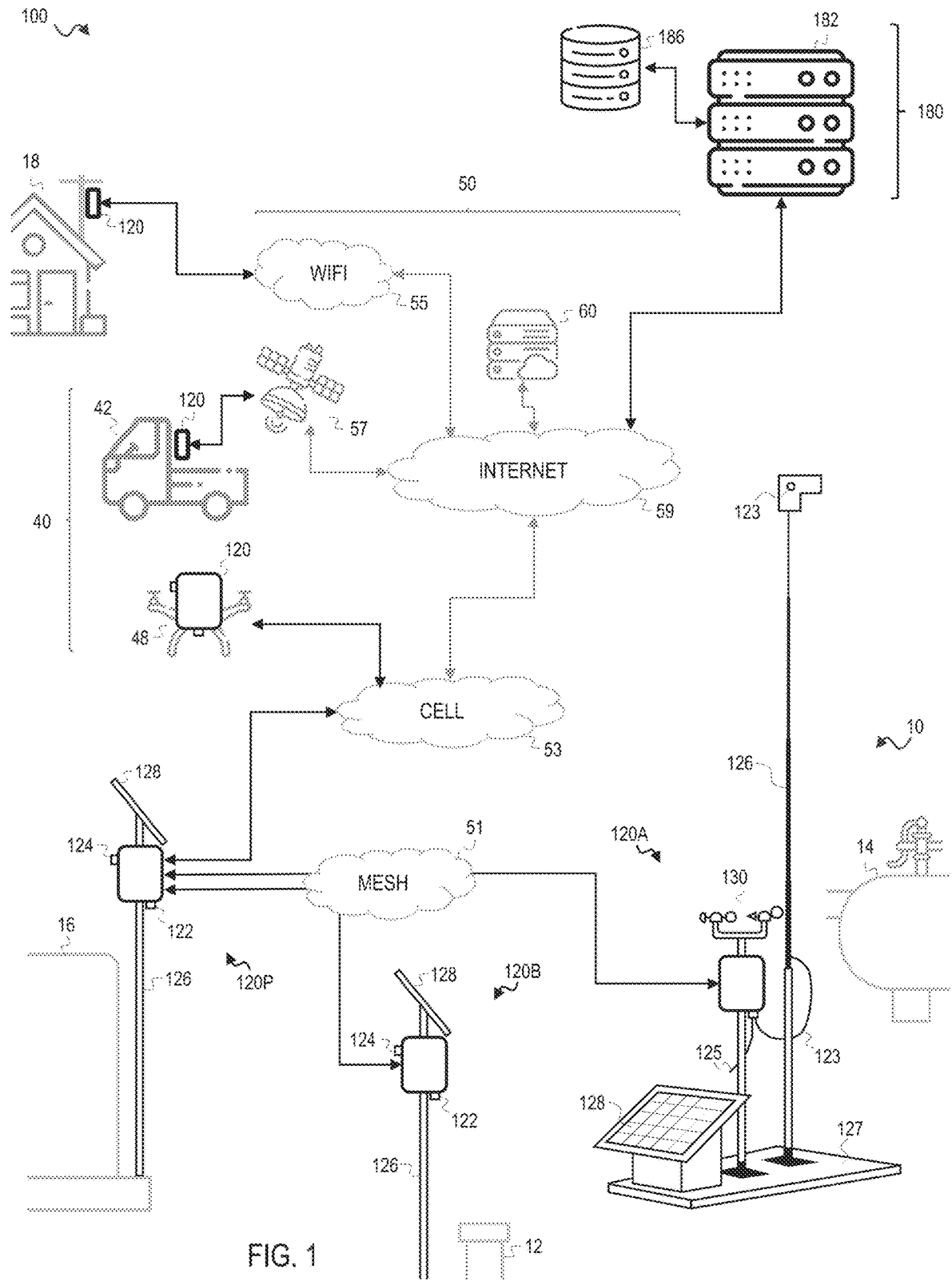
FIG. 1 is a diagram of a gas leak detection system, including sensor units deployed at a site and a remote data analysis and reporting system, according to an exemplary embodiment of the present invention.

Reference to the drawings illustrating various views of exemplary embodiments is now made. In the drawings and the description of the drawings herein, certain terminology is used for convenience only and is not to be taken as limiting the embodiments of the present invention. Furthermore, in the drawings and the description below, like numerals indicate like elements throughout.

Disclosed is a gas leak detection system 100 that combines sensor units having an array of sensors that detect natural gas and the volatile organic compounds and variable atmospheric conditions that confound existing gas leak detection methods, a specially designed sensor housing that limits the variability of those atmospheric conditions, and a machine learning-enabled process that uses the wide array of sensor data to differentiate between natural gas leaks and other confounding factors.

System Architecture

FIG. 1 is a diagram of a gas leak detection system 100 deployed at a site 10 according to an exemplary embodiment of the present invention. In the example embodiment of FIG. 1, the site 10 is an oil or natural gas well pad (e.g., a producing facility, a pre-production or early-production well pad, a plugged or abandoned or orphaned well pad, etc.) that includes a well head 12, a separator 14, a storage tank 16, etc., as well as a nearby neighborhood 18.

As shown in FIG. 1, the system 100 includes one or more sensor units 120 at each site 10, which are in communication with a data analysis and reporting system 180 via communication networks 50. For each site 10, the system 100 includes at least one anemometer 130 (e.g., Argent Data Wind Sensors) that measures the wind speed and direction at or near the site 10.

The data analysis and reporting system 180 includes at least one server 182 and non-transitory computer readable storage media 186. The server 182 may be any hardware computing device having a hardware computer processor capable of performing the functions described below. The data analysis and reporting system 180 may also receive data from one or more third party data sources 60 via the communications networks 50.

The communications networks 50 may include short-range wireless networks 51 (e.g., a mesh network formed by the sensor units 120 at the site 10), cellular networks 53, WiFi networks 55, satellite communications networks 57 (e.g., the Iridium Satcom system, SpaceX Starlink, etc.), and the Internet 59.

In some embodiments, some or all of the sensor units 120 deployed at the site 10 have a parent-child relationship, where secondary sensor units 120A and 120B output sensor data to a primary sensor unit 120P (e.g., using direct, short range, wireless communication) and the primary sensor unit 120P forwards the sensor data collected by both the primary sensor unit 120P and the secondary sensor units 120A and 120B to the data analysis and reporting system 180 (e.g., via a cellular network 53 or a WiFi network 55 and the Internet 59). In other embodiments, each of the one or more sensor units 120 deployed at the site 10 output sensor data to the data analysis and reporting system 180 directly (e.g., via a cellular network 53, a WiFi network 55, or a satellite communications network 57).

The sensor units 120, which are described in detail below with reference to FIGS. 2A-3E, collect air samples at the site 10, enabling the gas leak detection system 100 to detect gas leaks at the site 10. To do so, each sensor unit 120 includes an intake port 122 (e.g., a PVC pipe) and/or intake tube 123 for collecting air samples and an exhaust port 124 and/or exhaust tube 125 for exhausting those collected air samples. The ends of the intake tube 123 and the exhaust tube 125 may be protected within the larger intake port 122, which may include screens to protect the openings of the intake tube 123 and the exhaust tube 125 from dust, snow, insect nesting, etc.

Each sensor unit 120 includes a power source 128. In most embodiments, the power source 128 is a solar panel, enabling the sensor unit 120 to self-sufficiently operate in any location that receives light from the sun. In some instances, however, a sensor unit 120 may be used in a location with a consistent power source 128 (e.g., an AC power source, a vehicle or other battery, etc.).

To collect air samples above ground level, one or more of the sensor units 120 may include a mast 126. To collect air samples at a user-selectable height, the height of the mast 126 may be adjustable. In some embodiments, a sensor unit 120 may be mounted on the mast 126. The sensor units 120P and 120B of FIG. 1, for example, are shown mounted on metal masts 126, enabling sensor units 120P and 120B to collect air samples above ground level via an intake port 122. In other embodiments, a sensor unit 120 may be located near a mast 126 and include an intake tube 123 affixed to the mast 126 to collect air samples above ground level. In those embodiments, the mast 126 may be a light weight, insulative material (e.g., fiberglass) on a wide base 127 to prevent the mast 126 from being struck by lightning and to reduce the likelihood of the mast 126 being knocked over during a storm. In those embodiments, the mast 126 may also be hollow, enabling the intake tube 123 to be placed inside the mast 126. The sensor unit 120A of FIG. 1, for example, is shown mounted on a base 127 with a telescoping fiberglass mast 126, enabling a sensor unit 120A to collect air samples via the intake tube 123 extending to the top of the mast 126. In some embodiments, a sensor unit 120 may include two intake tubes 123, enabling the sensor unit 120 to collect air samples from two different heights (for example, at the top of the mast 126 and at the middle of the mast 126). In addition to increasing the likelihood that at least one of the intake tubes 123 will intercept the emissions plume of a gas leak, collecting spaced-vertically air samples helps to define the spatial distribution of gas within the plume, which can be used within a plume model (as described below with reference to FIGS. 6-17) to better define what the likely emissions rate is at the leak source.

The particular way that the sensor units 120 are deployed will depend on the structures on a particular site 10, how those structures are arranged on the site 10, and the typical wind conditions. Wind conditions (e.g., lack of winds) are an important factor in this consideration, since they transport trace gases from the gas leak to the sensor unit 120. Sites 10 where the wind direction varies relatively uniformly may allow for use of only a single sensor unit 120 in a central location relative to the structures on the site 10. In those instances, if the intake port 122 or the opening of the intake tube 123 is relatively high above ground, the centrally-located sensor unit 120 can rely on the different wind directions to advect gases to the sensor unit 120 from locations elsewhere on the site 10 and can detect gases released during calm conditions because the plume will rise nearly vertically and disperse laterally in a uniform way. If the wind direction at a site 10 tends to be distributed mostly only along two main axes, which is common, then two sensor units 120 would likely be needed, preferably arranged parallel to the prevailing wind direction. When wind directions are more variable, or when a site is particularly large, three or more sensor units 120 may be deployed.

As shown in FIG. 1, a sensor unit 120 may also be installed in a nearby neighborhood 18 (e.g., downwind of a potential gas source). In each instance, the sensor unit 120 may communicate via a WiFi network 55 if available or a cellular network 53 or satellite communications network 57 if a WiFi network 55 is unavailable.

A version of the sensor unit 120 may also be mounted on a vehicle 40, such as a motor vehicle 42 or (manned or unmanned) aircraft 48, for example if more in-depth spatial mapping of gas plume dimensions and characteristics is desired. That approach can be extended to combine a network of mobile sensor units 120 with readings available in real time at the data analysis and reporting system 180 (e.g., to direct sensor unit 120 operators to different locations to help pinpoint leak sources).

Sensor Suite

Figure 2A:
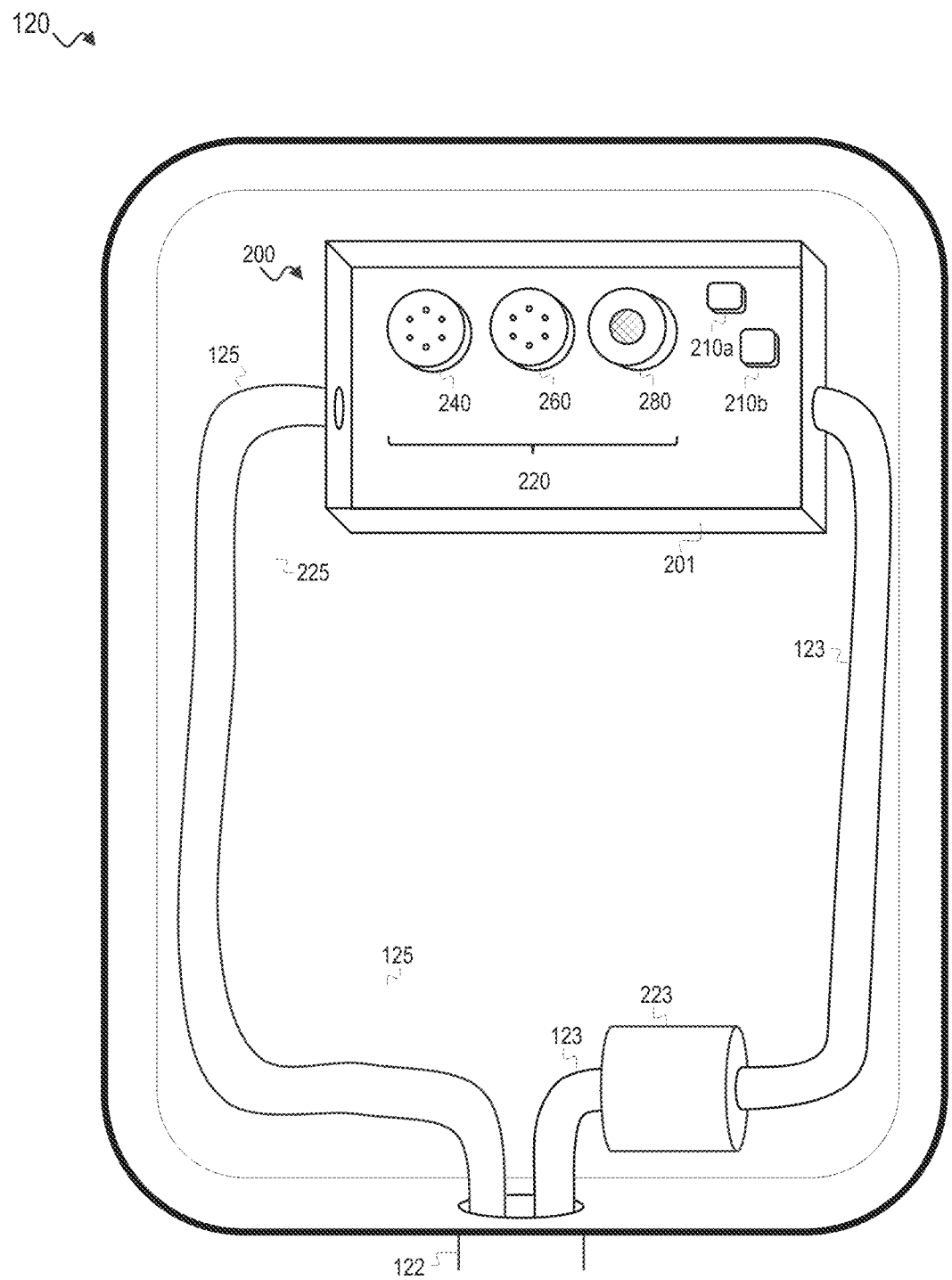
FIG. 2A is a diagram of a sensor suite of a sensor unit according to an exemplary embodiment.

FIG. 2A is a diagram of a sensor suite 200 of a sensor unit 120 according to an exemplary embodiment.

As described above, metal oxide gas sensors are inexpensive, durable, and are sufficiently sensitive to natural gases (methane, ethane) for emissions monitoring needs. However, the sensitivity of metal oxide sensors to natural gases is swamped by their sensitivity to volatile organic compounds that may also be present in the atmosphere. If the concentration of total volatile organic compounds (TVOCs) in an air sample could be accurately determined, their effect on the sensor data output by metal oxide gas sensors could be subtracted out. However, the presence of methane also reduces the sensitivity of VOC detectors (e.g., photoionization detectors). Therefore, existing methods have been unable to differentiate between changes in the sensor output of metal oxide gas sensors due to a natural gas leak and changes in that sensor output caused by the presence of volatile organic compounds.

The gas leak detection system 100 overcomes the drawback of cross-sensitivities to different gases by combining a machine learning-enabled gas leak detection process 400 (described below with reference to FIG. 4) and an array of metal oxide sensors 220 that each exhibit a different type and range of sensitivity to methane and volatile organic compounds. In the embodiment of FIG. 2A, the array of metal oxide sensors 220 includes a methane-sensitive metal oxide sensor (MOS) 240, a VOC-sensitive MOS 260, and a VOC-filtered MOS 280. The methane-sensitive MOS 240 may be any metal oxide sensor configured to output an indication of the concentration of methane in air samples (e.g., a Figaro TGS2600). The VOC-sensitive MOS 260 may be any metal oxide sensor configured to output an indication of the concentration of volatile organic compounds in air samples (e.g., a Figaro TGS2602). The VOC-filtered MOS 280 may be any metal oxide sensor that includes a volatile organic compound filter and outputs an indication of the concentration of methane and ethane in filtered air samples (e.g., a Figaro TGS2611). The volatile organic compound filter of the VOC-filtered MOS 280 may be any filter (e.g., a charcoal filter) that filters air samples and outputs filtered air samples having a lower concentration of volatile organic compounds than the unfiltered air samples.

Each of the metal oxide sensors 220 exhibit a different type and range of sensitivity to methane and volatile organic compounds. The methane-sensitive MOS 240 is sensitive to relatively low concentrations of methane in an air sample, but is affected by the presence of volatile organic compounds in the air sample. The VOC-sensitive MOS 260 is sensitive to volatile organic compounds in the air sample, but is affected by the presence of methane in the air sample. Because the VOC-filtered MOS 280 includes a volatile organic compound filter, it is significantly less sensitive to volatile organic compounds than the methane-sensitive MOS 240. However, increasingly larger amounts of VOC filtration also reduces methane sensitivity of the VOC-filtered MOS 280 relative to the methane-sensitive MOS 240.

Because each of the metal oxide sensors 220 exhibit a different type and range of sensitivity to methane and volatile organic compounds, the gas leak detection system 100 is able to separately determine the concentrations of both methane and volatile organic compounds. Using the machine learning-enabled gas leak detection process 400 described below, the gas leak detection system 100 can predict the response of the array of metal oxide sensors 220, assuming that no methane or VOCs are present in the air sample. The system 100 then calculates the difference between the sensor data output by the array of metal oxide sensors 220 in response to the air sample and that predicted response and converts the response difference to a measured concentration of methane and other gases.

Another drawback of metal oxide sensors discussed above is they are also sensitive to variations in the atmospheric conditions of the air sample (primarily the moisture content of the air sample and secondarily the temperature of the air sample). To remove the temperature and humidity effects from the sensor data output by the metal oxide sensors 220, the gas leak detection system 100 identifies the temperature and moisture content of the air sample, uses the machine learning-enabled gas leak detection process 400 described below to predict the sensor response of the array of metal oxide sensors 220 for the given temperature and moisture content of the air sample, calculates the difference between the sensor data output by the array of metal oxide sensors 220 and that predicted response, and converts the response difference to a measured concentration of methane and other gases.

To identify the temperature and moisture content of the air sample, the sensor suite 200 also includes at least one temperature and relative humidity sensor 210 configured to output indications of the temperature and relative humidity of the air samples (e.g., a Renesas HS3001). Given the importance of removing the temperature and humidity effects, preferred embodiments of the sensor suite 200 include at least two temperature and relative humidity sensors 210a and 210b, preferably with different sensitivity and response times. (For example, the sensor suite 200 may include both a Renesas HS3001 and a Bosch Sensortec BME680, which also outputs an indication of the concentration of volatile organic compounds in air samples). Those different sensitivities and response times help address the small mismatch in the response times of the metal oxide sensors 220 and the temperature and relative humidity sensors 210 to changes in temperature and humidity, improving the temperature and relative humidity correction performed by the system 100.

The sensor unit 120 also further reduces variations in the temperature and humidity of the air sample by enclosing the sensor suite 200 in a sealed sensor chamber 201 that is in flow communication with the intake tube 123 and the exhaust tube 125. The intake tube 123 includes a software-controlled intake pump 223 that introduces the air sample into the sensor chamber 201. The metal oxide sensors 220 generate heat as a natural byproduct of the air sampling process and heat the air sample. Because the sensor suite 200 is enclosed in a sealed sensor chamber 201, the temperature of the air sample is largely a function of the length of the exposure time period specified by the system 100 and is therefore less dependent on variations in the outside air temperature. Accordingly, the sensor unit 120 takes advantage of the heat generated by the metal oxide sensors 220 to provide a more consistent range of temperature and humidity conditions for the sampled air.

The length of the exposure time period is typically 10 seconds and can be selected to optimize system performance. Regardless of the selected length of the exposure time period however, sampling air at a site 10 over an exposure time period having a consistent length reduces the variability caused by changes in the outside air temperature and improves the performance of the metal oxide sensors 220.

To further reduce variations in the moisture content of the air samples, the intake tube 123 may have a moisture-blocking design and may pass the air samples through a desiccant material that reduces the moisture content of the air samples. The sensor chamber 201 (as well as the intake tube 123 and exhaust tube 125) may be a low-VOC material (e.g., Teflon) to minimize the amount of VOC outgassing, which could affect the output of the metal oxide sensors 220. In the embodiments described above where the sensor unit 120 includes two intake tubes 123 to collect air samples from two different heights, two intake pumps 223 are used, with air samples cycled alternately between intake tubes 123. In some embodiments, the sensor chamber 201 may also be configured to collect actual air samples for later analysis in a laboratory. For example, a microprocessor command to a servo may open an air inlet on a sample flask or bag (e.g., when the sensor unit 120 detects gas readings above certain levels). In those embodiments, for instance, the sensor unit 120 may alert the data analysis and reporting system 180 that an air sample had been collected and is available for pick-up and laboratory analysis.

As described above, the gas detection system 100 is able to differentiate between natural gas leaks and volatile organic compounds because, rather than relying on data from a single sensor, the sensor suite 200 captures datapoints from an array of metal oxide sensors 220 that each have a different responsiveness to methane and volatile organic compounds. Meanwhile, the responsiveness of each metal oxide sensor 220 to each particular gas varies depending on the temperature of the heater element of that metal oxide sensor 220. In some embodiments, the sensor unit 120 takes advantage of the temperature-dependent responsiveness of each metal oxide sensor 220 to collect even more datapoints that can be used by the system 100 to identify, quantify, and locate natural gas leaks. Specifically, in those embodiments, the sensor unit 120 heats and cools one or more of the metal oxide sensors 220 and collects the sensor data output by each metal oxide sensor 220 at different time periods when that metal oxide sensor 220 has been heated or cooled to a different temperature. Because the responsiveness of the metal oxide sensor 220 to each gas is different at each of those different temperatures, the sensor data from that metal oxide sensor 220 at those different time periods can effectively be treated as sensor data from separate sensors 220.

Figure 2D:
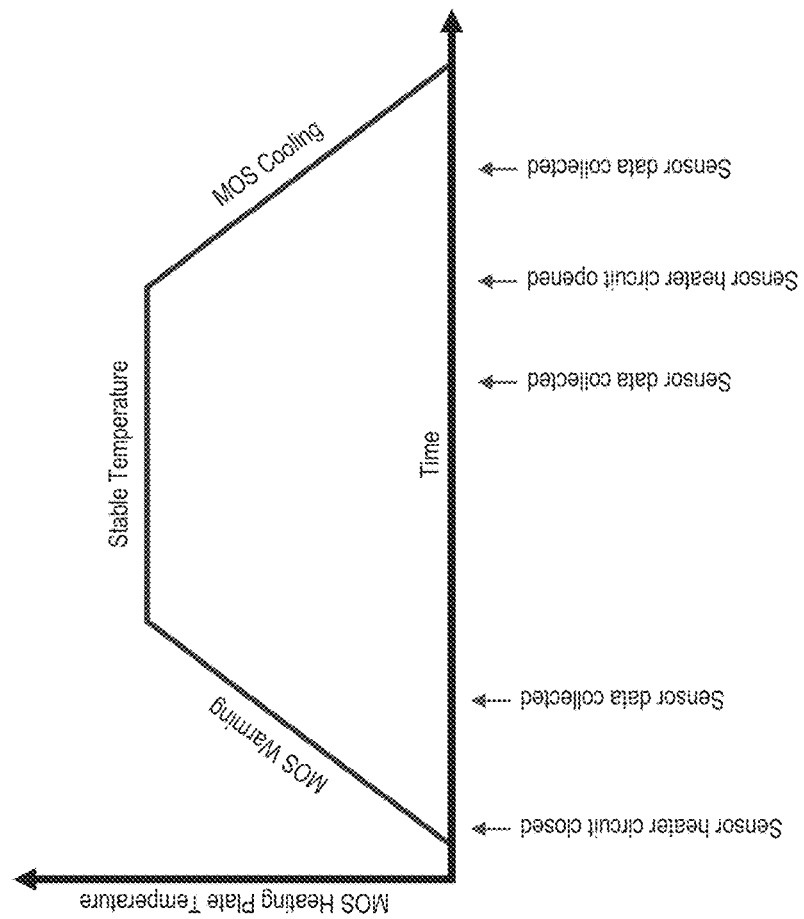
FIG. 2D is a graph depicting an active temperature modulation process according to an exemplary embodiment.
Figure 2B:
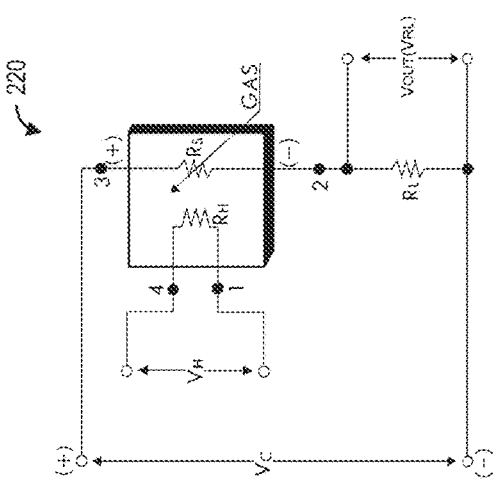
FIG. 2B is a diagram of the basic measuring circuit of a metal oxide sensor.

FIG. 2B is the basic measuring circuit of a metal oxide sensor 220. As shown in FIG. 2B, a circuit voltage $V_C$ (e.g., 5 volts DC) is applied across the sensor element, which has a resistance $R_S$ between the sensor's two electrodes and the load resistor $R_L$ connected in series. The sensor signal is measured indirectly as a change in voltage $V_{RL}$ across the load resistor $R_L$. A heater voltage $V_H$ is applied to a heating plate (e.g., an RuO2 heater), which heats the sensing material. Variation in the heater voltage $V_H$ changes the response of the sensor 220 to various gases. Therefore, the heater voltage $V_H$ is typically kept constant (e.g., 5.0V±0.2V AC or DC).

Figure 2C:
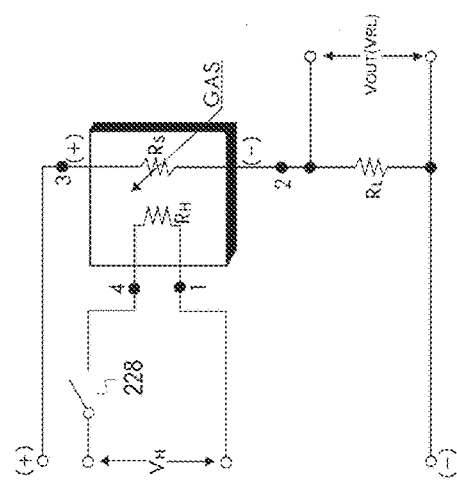
FIG. 2C is a diagram of a sensor heater circuit for a metal oxide sensor according to an exemplary embodiment.

FIG. 2C illustrates a sensor heater circuit 228 for a metal oxide sensor 220 according to an exemplary embodiment. As shown in FIG. 2C, the heating plate of the metal oxide sensor 220 is controlled by the sensor heater circuit 228. The sensor heater circuit 228 may be, for example, a MOSFET switch.

FIG. 2D is a graph depicting an active temperature modulation process according to an exemplary embodiment. In the embodiment of FIG. 2D, sensor heater circuit 228 is closed (e.g., in response to a command from a microcontroller), causing the heating plate of the metal oxide sensor 220 to heat. After a first predetermined time period, sensor data is collected from the metal oxide sensor 220 (the "ramp up" measurement) as the temperature of the metal oxide sensor 220 is increasing. After a second predetermined time period, sensor data is collected from the metal oxide sensor 220 (the "stable temperature" measurement) as the temperature of the metal oxide sensor 220 is stable. The sensor heater circuit is then opened, allowing the sensor metal oxide sensor 220 to cool. After a third predetermined time period, sensor data is collected from the metal oxide sensor 220 (the "ramp down" measurement) as the temperature of the metal oxide sensor 220 is falling. The sequence may then be repeated.

Switching the sensor heating plate on and off for predetermined time periods as described above yields three distinct time periods during which the response of the metal oxide sensor 220 may vary: one during the temperature rise, one during a stable temperature, and one during cooling. (In other embodiments, more complex thermal cycling may be employed, for example that yield sine wave or saw-tooth patterns of temperature variation.) For each of the metal oxide sensors 220 that is being cycled, the implementation described above would result in three individual resistances per time step, which can be viewed as equivalent to having three different sensors with slightly different sensitivities. In some embodiments, the number of distinct time periods may be limited to three to limit the extra data being transmitted to the data analysis and reporting system 180. In other embodiments, however, additional sensor data may be collected to better inform the automated classification methods described below.

Figure 2E:
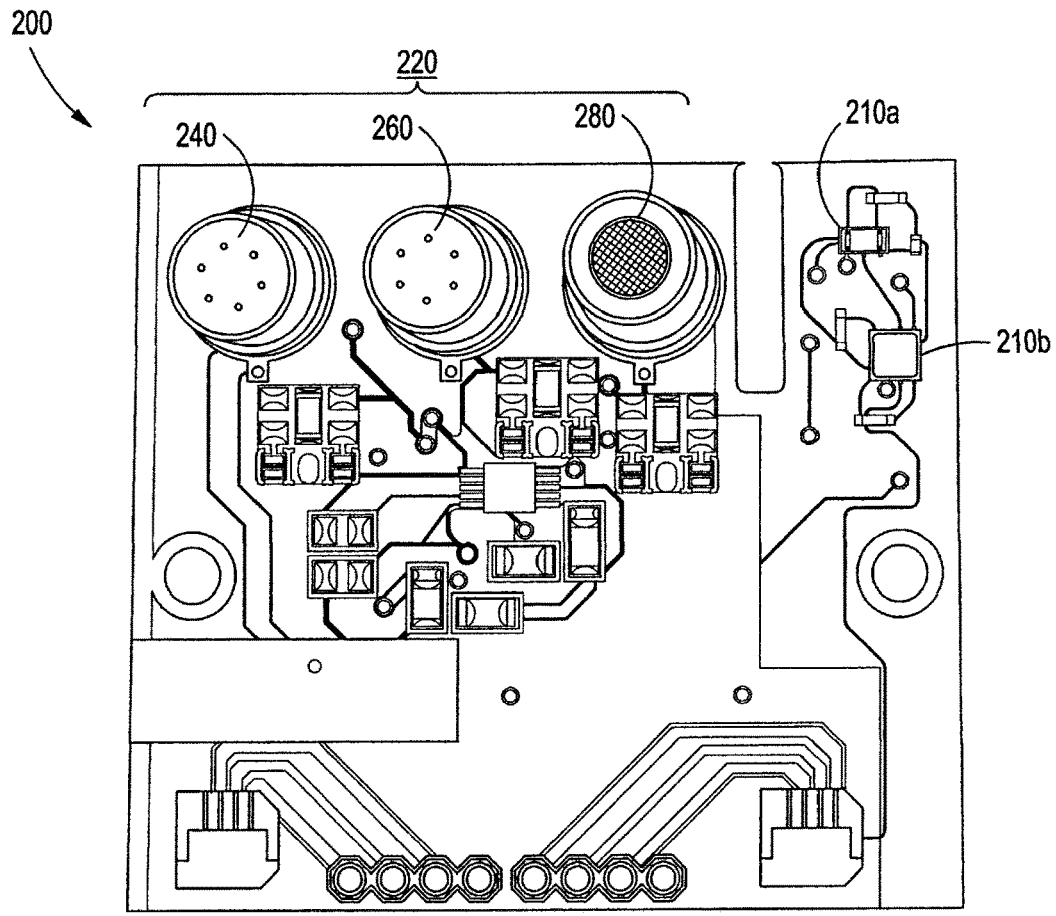
FIG. 2E is an image of the sensor suite of FIG. 2A according to an exemplary embodiment.

FIG. 2E is an image of the sensor suite 200 according to an exemplary embodiment. In the embodiment of FIG. 2E, the sensor suite includes the array of metal oxide sensors 220 (including the methane-sensitive MOS 240, the VOC-sensitive MOS 260, and the VOC-filtered MOS 280) as well as a temperature and relative humidity sensor 210.

Figure 2F:
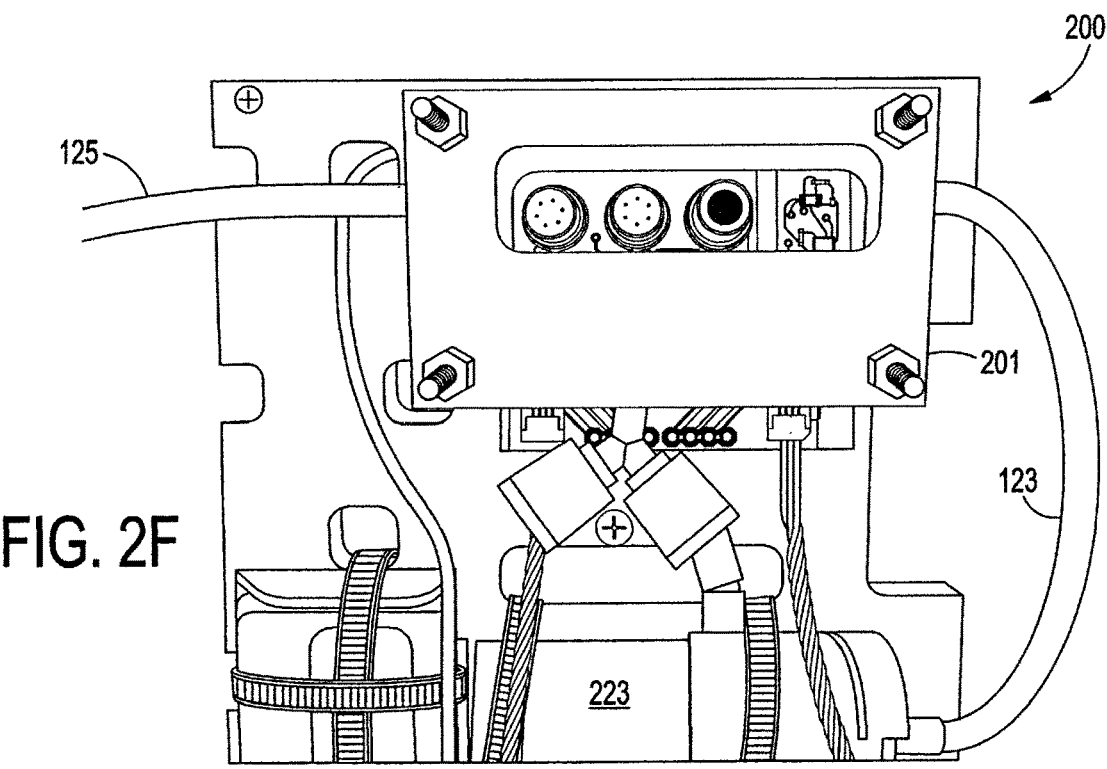
FIG. 2F is an image of the sensor suite of FIG. 2A inside a sealed sensor chamber according to an exemplary embodiment.

FIG. 2F is an image of the sensor suite 200 inside the sealed sensor chamber 201 according to an exemplary embodiment. As shown in FIG. 2F, the intake pump 223 introduces an air sample into the sensor chamber 201 via the intake tube 123, where the sensor suite 200 is exposed to the air sample for a predetermined sampling time period before the air sample is evacuated via the exhaust tube 125. As described above, the sealed sensor chamber 201 (and the heat generated by the metal oxide sensors 220) limit variations in the temperature and humidity of the air samples, enabling the system 100 to more accurately differentiate between natural gas leaks and unrelated variations in the atmospheric conditions at the site 10.

Sensor Unit

Figure 3A:
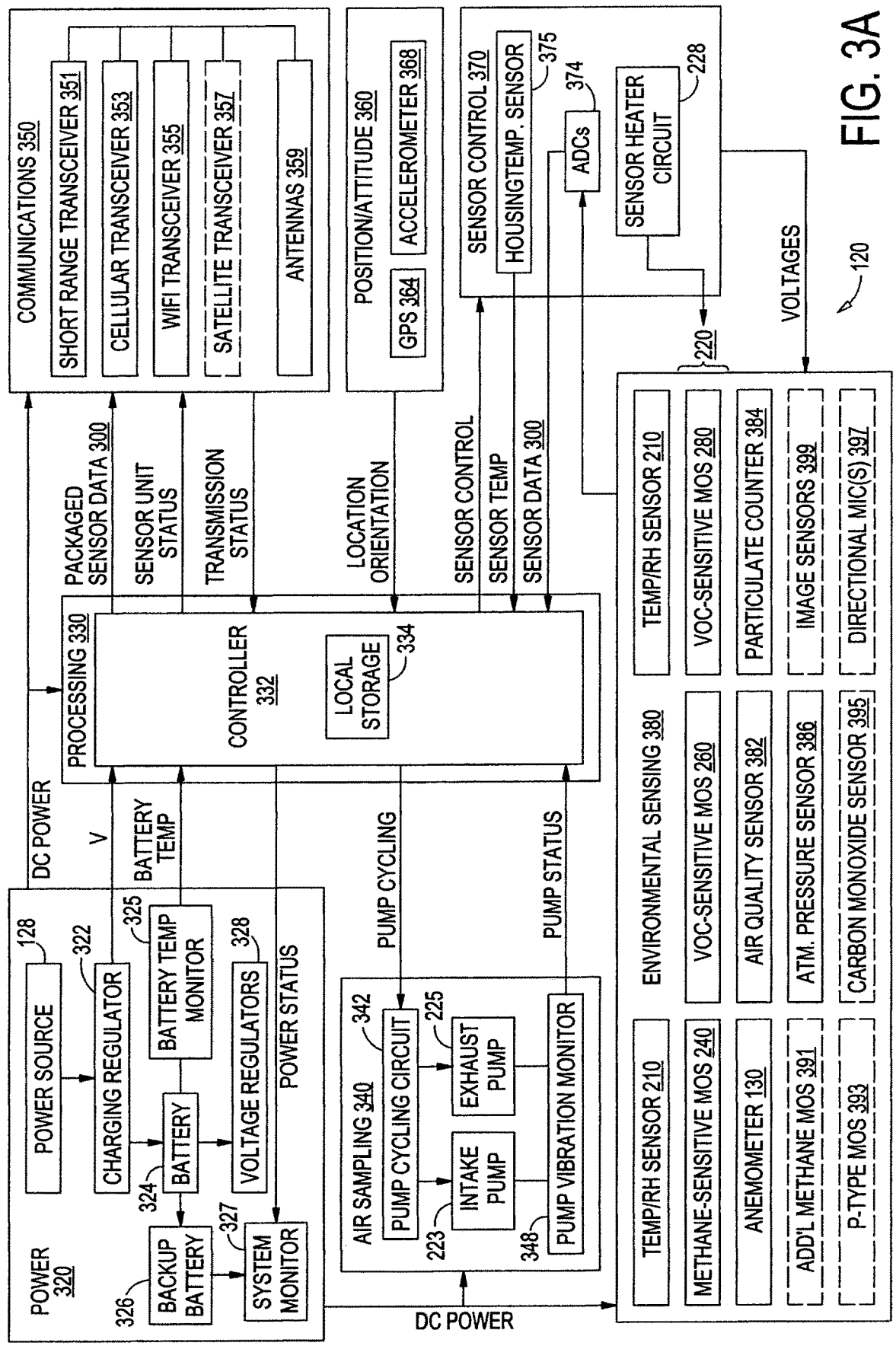
FIG. 3A is a block diagram of a sensor unit according to an exemplary embodiment.

FIG. 3A is a block diagram of the sensor unit 120 according to an exemplary embodiment. In the embodiment of FIG. 3A, the sensor unit 120 includes a power subsystem 320, a processing subsystem 330, an air sampling subsystem 340, a communications subsystem 350, a position/attitude subsystem 360, a sensor control subsystem 370, and an environmental sensing subsystem 380.

The processing subsystem 330 includes a controller 332 and local storage 334. The local storage 334 may be any non-transitory computer readable storage media (e.g., a microSD card). The controller 332 may include any hardware processing unit capable of performing the functions described herein. For example, the controller 332 may be a flash microcontroller (e.g., a Microchip Technology SAMD21). The controller 332 may also include additional hardware processing units (e.g., dedicated hardware configured to perform one or more of the specific functions described herein). To send and receive data from other subsystems, the controller 332 may include a universal asynchronous receiver/transmitter (UART), analog-to-digital converters (ADCs), digital-to-analog converters (e.g., to output data to external devices), and digital and/or analog ports. The controller 332 may also communicate with other subsystems using the Inter-Integrated Circuit (I2C) serial communication protocol, the Serial Peripheral Interface (SPI) communication protocol, etc.

As described below, the processing subsystem 330 receives sensor data 300 from the environmental subsystem 380 (via the sensor control subsystem 370), packages that sensor data 300, logs the packaged sensor data 300 in the local storage 334, and outputs the packaged sensor data 300 to the data analysis and reporting system 180 via the communications subsystem 350.

The power subsystem 320 receives power from the power source 128 (e.g., solar panel or AC power source), stores that power in a battery 324, and provides DC power to each of the other subsystems. To do so, the power subsystem 320 includes a charging regulator 322 that regulates the power received from the power source 128, and voltage regulators 328 that provide DC power at the voltage level required by each component. The storage capacity of the battery 324 and the power source 128 (e.g., the size of the solar panel and resulting current output) may be selected as appropriate for the site 10.

In embodiments where the power source 128 is a solar panel, the charging regulator 322 may include a high definition voltage divider that allows the controller 332 to track the voltage output by the solar panel, including spikes caused by great amounts of sunlight. The power subsystem 320 also includes a battery temperature monitor 325 that detects overheating of the battery and outputs an alert to the controller 332.

The voltage regulators 328 may include a power smoothing system that reduces noise in the power signal. In embodiments where the power source 128 is provided at the site 10, most of the components of the power subsystem 320 (with the exception of power regulation and conditioning) may be replaced by a voltage regulator (for example, to reduce the voltage of a 12-volt DC power source 128 to 3.3 volts) or an AC-to-DC converter (for example, where the power source 128 is an AC power source).

The sensor unit 120 also includes a backup battery 326 (e.g., a 800 mAh lipo battery), which is continuously charged by the main battery 324, that supplements the battery 324 during processes that require higher amounts of power (e.g., cellular transmission). The backup battery 326 also provides power to a system monitor 327, a microcontroller (e.g., a Microchip Technology ATtiny) that protects the sensor unit 120 in situations in which the main battery 324 does not provide sufficient power to the sensor unit 120. In the embodiment of FIG. 3A, for instance, the controller 322 regularly outputs a power status update to the system monitor 327 indicating that the sensor unit 120 has sufficient power. If the system monitor 327 does not receive a power status update from the controller 322 for a predetermined time period (e.g., 2 minutes), the system monitor 327 is configured to reset each subsystem of the sensor unit 120, including the controller 332 and the communications subsystem 350. If the battery 324 cannot supply sufficient power to the sensor unit 120, the system monitor 327 outputs control signals to the other subsystems to enter a low power mode ("sleep mode") until the battery 324 is adequately charged by the power source 128. Powered by the backup battery 326, the system monitor 327 is configured to cause the other subsystems to resume normal operation once sufficient power is restored. Accordingly, the sensor unit 120 is self-powered and is able to adapt and automatically recover from insufficient power.

The air sampling subsystem 340 includes a pump cycling circuit 342 that controls the intake pump 223 to draw outside air into the sensor chamber 201 in response to pump cycling control signals output by the controller 332. The controller 332 initiates air sampling cycles at a preprogrammed sampling rate. However, in the event that the battery 324 is low on power, the controller 332 is configured to reduce that sampling frequency to conserve power until the battery 324 is adequately charged by the power source 128. Additionally, in cases of extreme environmental conditions such as excessive cold or heat, the controller 332 can pause the air intake cycle to minimize stress on pumps and other components.

The air sampling subsystem 340 also includes a pump vibration monitor 348 (e.g., a MEMS microphone) that outputs information indicative of the vibration of the intake pump 223, enabling the controller 332 to monitor the status of the intake pump 223.

The position/attitude subsystem 360 outputs information indicative of the location and orientation of the sensor unit 120 to the controller 332. The position/attitude subsystem 360 includes a global positioning system (GPS) receiver 364 and a 3-axis accelerometer 368. The GPS receiver 364, which may be incorporated in the cellular transceiver 353 or may be a stand-alone GPS receiver 364, outputs information indicative of the location of the sensor unit 120. The cellular transceiver 353 or GPS receiver 364 also outputs a clock signal used by the controller 332. The accelerometer 368 outputs information indicative of the orientation of the sensor unit 120, enabling the controller 332 to determine whether the mounting structure of the sensor unit 120 has shifted position or angle, which may occur under extreme winds.

The communications subsystem 350 outputs the packaged sensor data 300 received from the controller 332 to the data analysis and reporting system 180 and reports the transmission status to the controller 332. In the embodiment of FIG. 3A, the communications subsystem 350 includes a short-range wireless transceiver 351 for wirelessly communicating with other sensor units 120 (e.g., forming the mesh network 51 shown in FIG. 1), a cellular transceiver 353 for communicating via cellular networks 53, a WiFi transceiver 355 for communicating via WiFi networks 55, and a satellite transceiver 357 for communicating via satellite communications networks 57. Each of the transceivers includes an antenna 359. The short-range wireless transceiver 351 may be a XBEE3 Radio, which communicates using the IEEE 802.15.4 wireless protocol. The cellular transceiver 353 may use an Internet of Things (IoT) SIM card that specializes in small and remote data packets. The WiFi transceiver 355 may be a single-board computer (e.g., a Raspberry Pi) that uses the same antenna structure as the cellular transceiver 353.

As described above, in some embodiments, the sensor units 120 form a parent-child relationship where a primary sensor unit 120 sends call-and-response attempts via the short-range wireless transceiver 351 to trigger and receive the packaged sensor data 300 from secondary sensor units 120. Each short-range wireless transceiver 351 may utilize a high-powered antenna 359 with a 12 foot antenna height. The sensor units 120 employ a rapid-fire call-and-response system developed by Earthview to help maintain wireless communication on sites 10 with a lot of vehicle traffic that can otherwise disrupt wireless signals. When the sensor units 120 form a parent-child relationship, the primary sensor unit 120 forwards the packaged sensor data 300 collected by both the primary sensor unit 120 and secondary sensor units 120 to the data analysis and reporting system 180. In other embodiments, each sensor unit 120 outputs the packaged sensor data 300 to the data analysis and reporting system 180 directly.

The sensor unit 120 outputs the packaged sensor data 300 to the data analysis and reporting system 180 using calls to an application programming interface (API). In most instances, the cellular transceiver 353 outputs the packaged sensor data 300 by making the call to the API. If a WiFi network 55 is available at the site 10, the WiFi transceiver 357 (e.g., a Raspberry Pi) makes automated API calls (e.g., with a python script). When communicating via a WiFi network 55, the sensor unit 120 and the data analysis and reporting system 180 use a call-and-response system, enabling the sensor unit 120 to detect a failure to communicate via the WiFi network 55. If the WiFi transceiver 357 is unable to successfully transmit the packaged sensor data 300 to the data analysis and reporting system 180 via the WiFi network 55 for a predetermined time period (e.g., 2 seconds), the sensor unit 120 outputs the packaged sensor data 300 via the cellular transceiver 353. The cellular transceiver 353 also outputs custom responses to update the data analysis and reporting system 180 on conditions such as WiFi network 55 outages, lack of power to the WiFi transceiver 357, and program failures. The sensor unit 120 can also operate in extremely remote settings because the satellite transceiver 357 communicates via a satellite communications network 57 (e.g., an Iridium Satcom system) that is available anywhere on Earth with a view to the sky. Finally, even if the sensor unit 120 is in a location with no communications network, the packaged sensor data 300 is logged in the local storage 334, enabling the packaged sensor data 300 to be collected for analysis.

The controller 332 also outputs the status of the sensor unit 120 to the data analysis and reporting system 180 via the communications subsystem 350, enabling the status sensor unit 120 to be remotely monitored. The status of the sensor unit 120 may include, for example, the voltage output by the solar panel (determined using the charging regulator 322), the temperature of the battery 324 (determined by the battery temperature monitor 325), the status of the intake pump 223 (determined using the pump vibration monitor 348), and the orientation of the sensor unit 120 (determined by the accelerometer 368). Based on the orientation of the sensor unit 120, the data analysis and reporting system 180 may output an alert (e.g., by email) if a sensor unit 120 has been knocked on its side by strong winds.

The environmental sensing subsystem 380 includes the temperature and relative humidity sensor(s) 210 and the metal oxide sensors 220 described above with reference to FIG. 2A and the anemometer 130 described above with reference to FIG. 1. (Because only one anemometer 130 is required at or near each site 10, some sensor units 120 may not include an anemometer 130.) Additionally, in the embodiment of FIG. 3A, the sensor unit 120 also includes an outdoor air quality sensor 382 (e.g., a Renesas ZMOD4510 gas sensor platform). In some embodiments, the sensor unit 120 may include (e.g., outside the sensor chamber 201) one or more particulate counters 384 (e.g., Plantower PM2.5 and PM10 particulate matter sensors) and/or an atmospheric pressure sensor 386.

As described below with reference to FIG. 4, one benefit of the machine learning-enabled gas leak detection process 400 is that additional data can easily be incorporated to improve the accuracy of the gas leak detection system 100. Meanwhile, the sensor suite 200 is expandable (e.g., a separate, detachable module to allow more installation flexibility) to accommodate any number of additional sensors (including sensors developed in the future). Accordingly, in some embodiments, the sensor suite 200 may include (e.g., inside the sensor chamber 201) an additional methane-sensitive MOSs 391 (e.g., a Renesas SGAS711 solid-state chemiresistor sensor), a p-type metal oxide sensor 393 (e.g., an Alphasense p-type metal oxide sensor), which are less sensitive to variations in temperature and relative humidity than n-type metal oxide sensors, and/or a carbon monoxide sensor 395 (e.g., a Figaro TGS5141-P00 carbon monoxide gas sensor).

Another benefit of the machine learning-enabled gas leak detection process used by the gas leak detection system 100 is that it can incorporate sensor data 300 that would not be obviously associated with leak detection but that provides added machine-learning power for extracting leak-related signals. For example, in some embodiments, the environmental sensing subsystem 380 may include image sensors 397 and/or directional ultrasonic microphones 399. The directional ultrasonic microphones 399 may be used to detect sound emitted by leaking components and determine the direction of the gas leak relative to the sensor unit 120. Finally, because the data analysis and reporting system 180 can also incorporate data indicative of vibration or sound that is within human hearing range, the output of the pump vibration monitor 348 may be output as part of the packaged sensor data 300 used to detect gas leaks.

The sensor control subsystem 370 supplies a voltage to the sensors of the environmental sensing subsystem 380, includes analog-to-digital converters (ADCs) 374 that convert analog voltages output by the sensors of the environmental sensing subsystem 380 to digital sensor data 300, and outputs the digital sensor data 300 to the controller 332. (To convert the data output by the anemometer 130 to a signal that the controller 332 can interpret, the sensor control subsystem 370 may also include drop down resistors, filter capacitors, etc.) Because the responsiveness of the metal oxide sensors 220 to specific gases is dependent on the temperature of those metal oxide sensors 220, the sensor control subsystem 370 also includes a sensor housing temperature sensor 372 that monitors the external temperature of the housing of at least one of the metal oxide sensors 220 (e.g., using a thermistor), which is included in the sensor data 300.

As described above with reference to FIGS. 2C-2D, in some embodiments the sensor unit 120 improves instrument sensitivity and gas selectivity by actively modulating the temperature of the heating plate of one or more of the metal-oxide sensors 220. In those embodiments, for each metal oxide sensor 220 being heated, the sensor control subsystem 370 includes a sensor heater circuit 228 that controls the sensor heating plate in response to sensor control signals output by the controller 332.

Figure 3C:
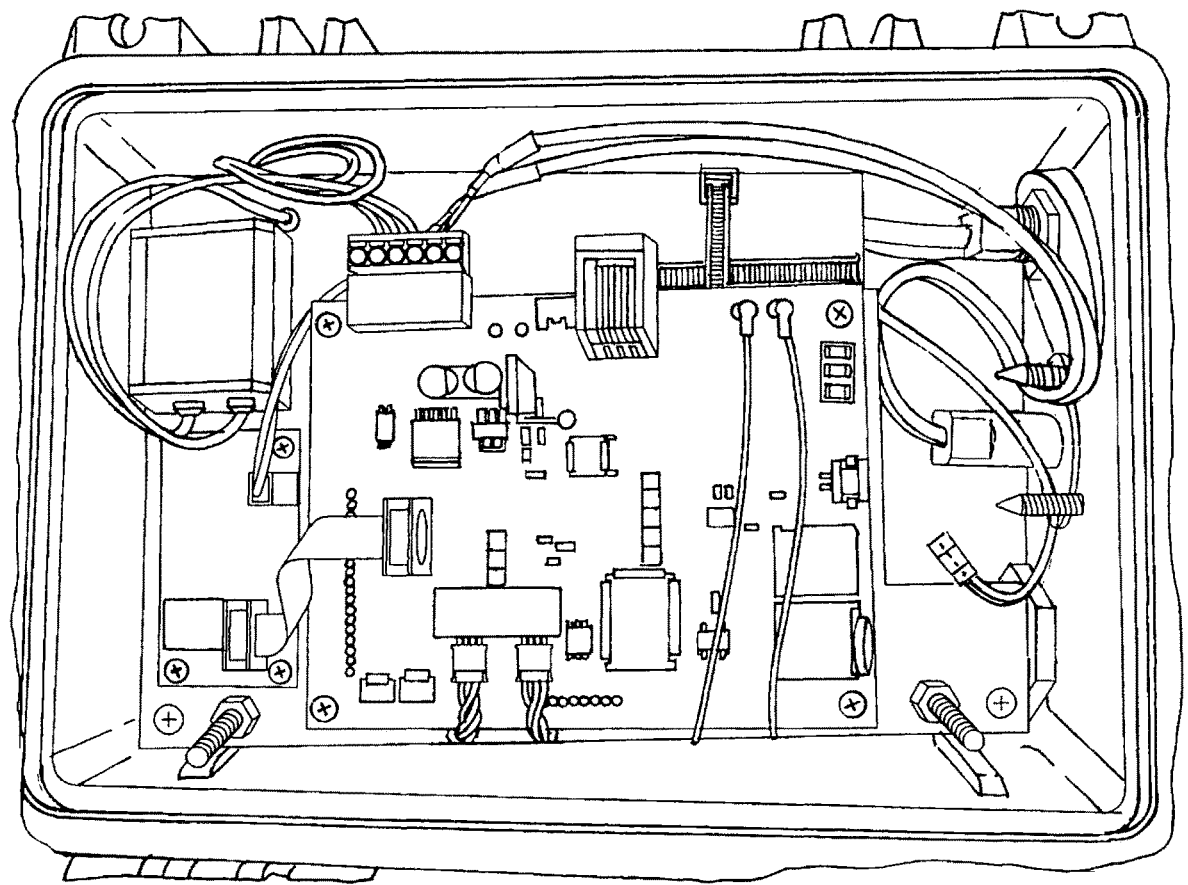
FIG. 3C is an interior view of the sensor unit according to an exemplary embodiment.
Figure 3B:
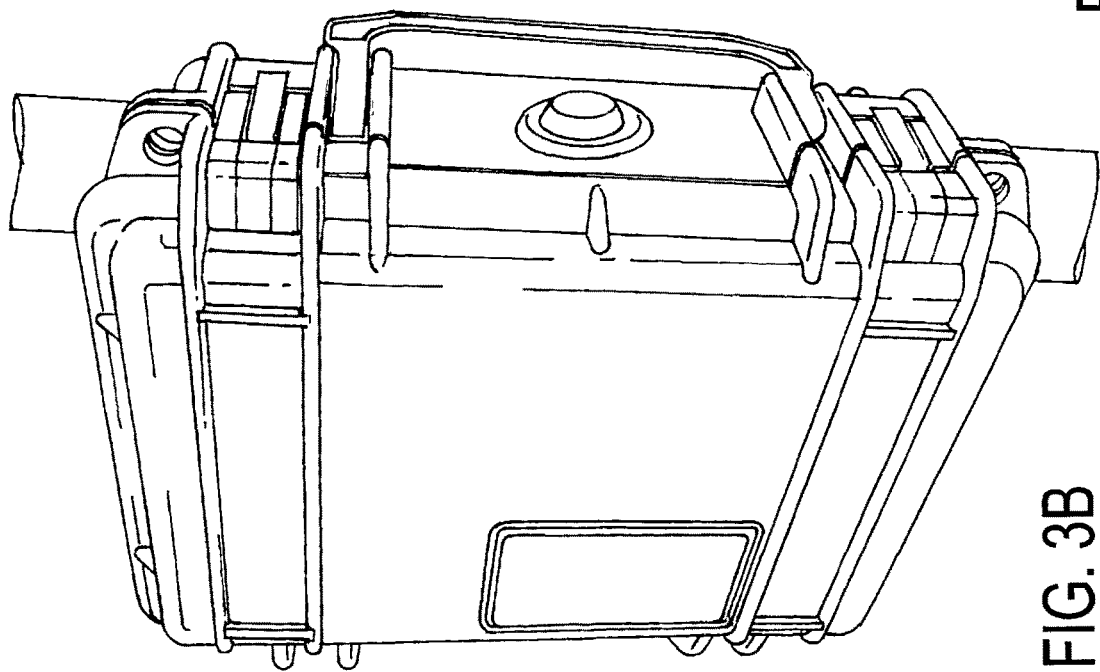
FIG. 3B is an exterior view of the sensor unit according to an exemplary embodiment.

FIG. 3B is an exterior view of the sensor unit 120 according to an exemplary embodiment. FIG. 3C is an interior view of the sensor unit 120 according to an exemplary embodiment.

Machine Learning-Enabled Gas Leak Detection Process

Figure 4:
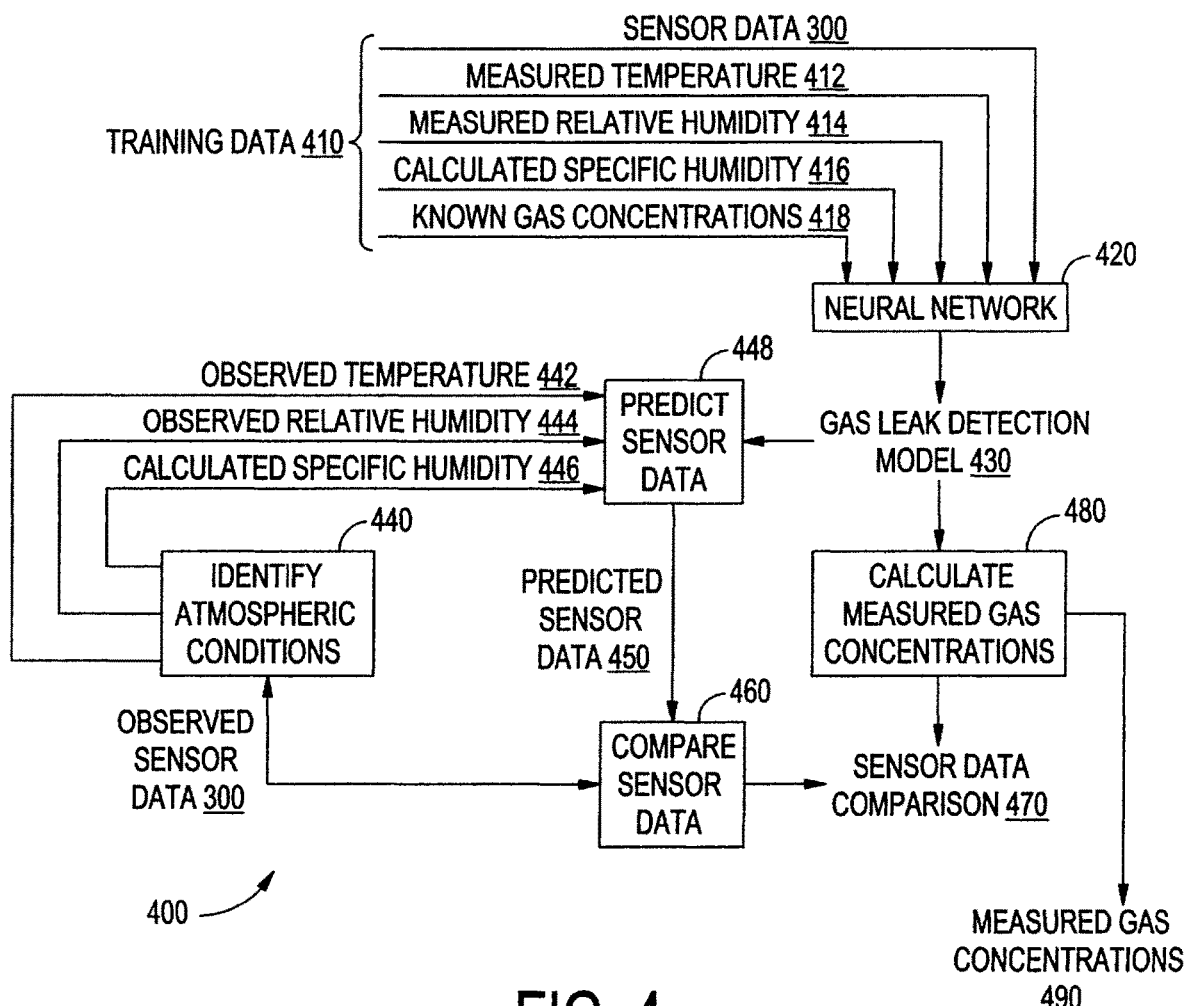
FIG. 4 is a flowchart illustrating a gas leak detection process according to an exemplary embodiment.

FIG. 4 is a flowchart illustrating a gas leak detection process 400 according to an exemplary embodiment.

The gas leak detection system 100 generates a gas leak detection model 430 indicative of the relationship between the sensor data 300 generated by the sensor unit 120, the atmospheric conditions in the location of the sensor unit 120, and the concentrations of methane and other gases. In the embodiment of FIG. 4, the gas leak detection model 430 is generated by training a forward-learning neural network 420 using training data 410 that includes sensor data 300 generated using the sensor unit 120 in locations with known concentrations 418 of methane and other gases, and the measured temperature 412 and measured relative humidity 414 in those locations. For instance, the training data 410 may be collected in laboratory experiments using both the sensor unit 120 and a reference-grade gas analyzer. Additionally or alternatively, the model may be generated by installing a sensor unit 120 adjacent to air quality monitoring stations.

Among environmental conditions, the metal oxide sensors 220 are most affected by the actual amount of water in the air, which influences the responsiveness of the metal-oxide sensor material to target gases. Therefore, the specific humidity 416 (i.e., the mass of water vapor per unit mass of air) is calculated to serve as an additional variable. In addition to affecting relative humidity 414, the air temperature 412 also affects the temperature of the housings of the metal oxide sensor 220, which in turn also affects the response of the metal oxide sensors 220. Even though the relative humidity 414 is a function of air temperature 412 and the specific humidity 416, it retains some predictive power and is therefore included in the training data 410 used to train the model 430.

The gas leak detection model 430 is then used to calculate measured gas concentrations 490 at a site 10 that includes a sensor unit 120.

When sensor data 300 is observed by a sensor unit 120, the atmospheric conditions in the location of the sensor unit 120 are determined in step 440, including the temperature 442 and relative humidity 444 observed by the temperature and humidity sensors 210 and the specific humidity 446 calculated using the observed temperature 442 and the observed relative humidity 444. The gas leak detection model 430 is used in step 448 to generate the predicted sensor data 450 that would be generated by the sensor unit 120 in those observed atmospheric conditions assuming that no methane or gases are present in the air sample. In step 460, the observed sensor data 300 is compared to the predicted sensor data 450 to generate a sensor data comparison 470. In preferred embodiments, the sensor data comparison 470 is generated by dividing the observed sensor data 300 by the predicted sensor data 450. (In other embodiments, the sensor data comparison 470 may be generated by performing a different comparison, such as calculating the difference between the observed sensor data 300 and the predicted sensor data 450.)

Because the gas leak detection model 430 is generated using training data 410 that includes known gas concentrations 418, the gas leak detection model 430 can be used to identify events in the sensor data 300 that best match the sensor data 300 gathered in the presence of natural gas. Additionally, the gas leak detection model 430 provides the ability to attribute sensor data 300 to the presence of other gases. Accordingly, in step 480, measured gas concentrations 490 are calculated using the sensor data comparison 470 and the gas leak detection model 430.

In other embodiments, the gas leak detection model 430 may be generated by extracting a time series from a moving time window of sensor data 300 and using that time series to calculate a non-linear (second order) multiple regression fit between the sensor data 300 (the dependent variable, or predictand) and the measured air temperature 412, the measured relative humidity 414, and the calculated specific humidity 416 (as the predictor variables). However, the forward-leaning neural network 420 described above has the advantage of computational efficiency. Once trained, the neural network 420 can be applied to each new observation in near real-time. Another advantage of a forward-leaning neural network 420 is that it is easier to make use of a larger set of inputs, such as using multiple temperature and humidity sensors 210, collecting multiple data points from metal oxide sensors 220 during the active temperature modulation process (described above with reference to FIGS. 2C-2D), and using sensor data 200 from directional microphones 397, the pump vibration monitor 348, an additional methane sensor 391, a p-type metal oxide sensor 393, etc.

As described above, while metal oxide sensors are sufficiently sensitive to natural gases for emissions monitoring needs, that sensitivity is swamped by their sensitivity to volatile organic compounds that may be present in the atmosphere, variations in the atmospheric moisture content and temperature, and the temperature of the sensor housing itself. The gas leak detection system 100 overcomes that drawback by training the neural network 420 on sensor data 300 from an array of metal oxide sensors 220 with different responses to different gases, one or multiple temperature and relative humidity sensors 210, and a housing temperature sensor 372. Meanwhile, the sensor units 120 are exposed to a variety of known gas concentrations 418. As a result, the training data 410 used to train the neural network 420 includes a set of multi-sensor signatures that represent the effects of different gas concentrations 418, which are captured in the gas leak detection model 430. When ultrasonic microphones 397 or image sensors 399 are included in the sensor data, the sounds or images are treated as an additional sensor input. Similarly, vibration sensed by the pump-vibration monitor 348 is treated as additional information. When active temperature modulation is used (as described above with reference to FIGS. 2C-2D), the resulting feature space data are classified using multivariate analysis methods.

Complementing this signature-capturing feature is the ability to use other sensor data 300 to help categorize what might be going on at a monitoring site 10 that could also affect the sensor data. For example, the measured gas concentrations 490 generated using the gas leak detection model 320 might indicate a best match with an indistinct hydrocarbon and carbon monoxide signature pattern. By using artificial intelligence-type if-then comparisons, the gas leak detection system 100 can check to see if there are concurrent elevated readings in particulates (as determined, for example, by the particulate counter 384) and vibration (as determined, for example, by the pump vibration monitor 348). If so, the gas leak detection system 100 can flag the event as being potentially due to the nearby operation of vehicles or other heavy equipment rather than an emissions event.

Accordingly, the gas leak detection system 100 capitalizes on the benefits of the types of sensors used in the sensor suite 200 while addressing their inherent limitations using sensor fusion and artificial intelligence steps. Meanwhile, by using a remote data analysis and reporting center 180, where sophisticated classification and feature extraction tools can be applied and revised over time, the gas leak detection system 100 can provide additional data post processing for feature extraction, leak detection, and gas concentration measurement.

As described above, another drawback of metal oxide sensors 220 is that they suffer from degradation and/or a change in sensor response over time. A common solution for gas sensors that experience degradation or sensor drift is to frequently calibrate those sensors using test gasses, which requires field visits or returning the instrument to the manufacturer. Another benefit of the gas leak detection process 400 is that addresses degradation and sensor drift without requiring calibration using test gasses. First, because the sensor data comparison 470 is normalized by ratioing the predicted sensor data 450 and the observed sensor data 300, with the predicted sensor data 450 calculated based on the observed atmospheric conditions, drift in the metal oxide sensors 220 becomes a non-factor. Second, atmospheric water vapor can be essentially treated as a calibration gas to which the metal oxide sensors 220 are continuously exposed. As described above, the neural network 420 models the response of the metal oxide sensors 220 to water vapor (the specific humidity 414), the temperature and humidity sensors 210 measure the specific humidity 414 in the air samples continually throughout the deployment of the sensor unit 120, and the expected sensor response to the amount of water vapor present (the predicted sensor data 450) is routinely calculated. Therefore, by comparing the sensor response to water vapor over time to the response seen after initial deployment, sensor degradation and sensor drift is quantified and a determination is made as to when a sensor 220 has become insufficiently responsive and requires replacing.

The training data 410 is stored by the data analysis and reporting system 180 (e.g., in the storage media 186) and the gas leak detection model 430 is generated by the server 182. In some embodiments, the sensor unit 120 outputs the packaged sensor data 300 to the data analysis and reporting system 180 (as described above with reference to FIG. 3A), which generates the measured gas concentrations 490. In other embodiments, the sensor unit 120 stores the gas leak detection model 430 (e.g., in the local storage 334).

In those embodiments, the controller 332 may use the gas leak detection model 430 to generate the predicted sensor response 450 for the observed atmospheric conditions, compare the observed sensor data 300 to the predicted sensor data 450, and convert the sensor data comparison 470 to measured gas concentrations 490. In those embodiments, the gas leak detection model 430 may be stored in the local storage 334 at the time of manufacture and updated over time, for example by the server 182 updating the firmware over a network 50.

In other embodiments, the local controller 332 may generate coarse gas concentration measurements and the server 182 may generate finer, more accurate measurements. To reduce the amount of data transferred, for example, the local controller 332 may generate coarse measurements at a higher sampling rate than the server 182 and the server may generate more accurate measurements at a lower sampling rate than the local controller 332. In another example, the local controller 332 may generate a number of measurements and periodically output the maximum and average measured gas concentrations 490 generated over a predetermined time interval.

Results

Figure 5A:
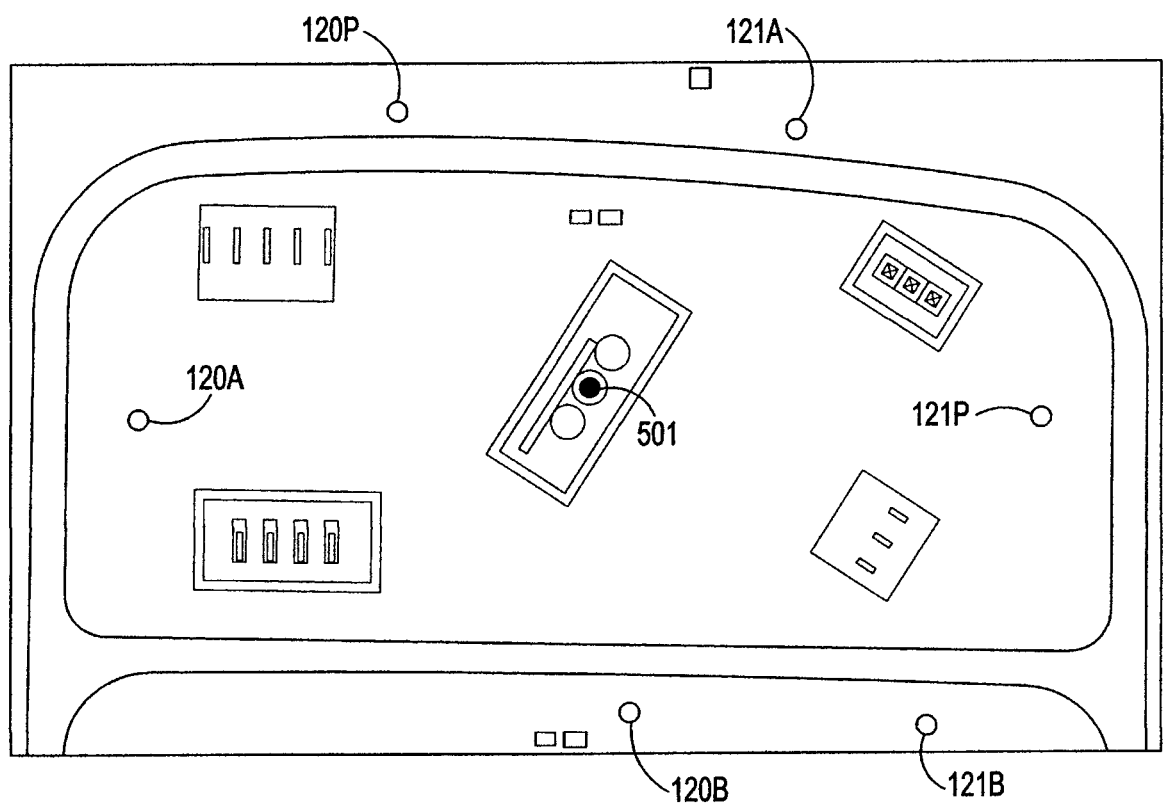
FIG. 5A is an image that depicts the gas leak detection system deployed for methane emissions testing and evaluation.

FIG. 5A depicts the gas leak detection system 100 deployed for methane emissions testing and evaluation by the Methane Emissions Technology Evaluation Center (METEC) under a variety of weather conditions and gas release rates. Two gas leak detection systems 100 were deployed. The first gas leak detection system 100 included a primary sensor unit 120P, and two secondary sensor units 120A and 120B. The second gas leak detection system 100 included a primary sensor unit 121P, and two secondary sensor units 121A and 110B. As shown in FIG. 5A, METEC released methane from one source 501 at various times and at various emission rates throughout the day and night. The times of gas emission and the emission rates were never shared during the testing and were only obtained once measured gas concentrations 490 were submitted to METEC at the conclusion of the test. The weather during the test varied wildly and included high winds, a light blizzard, low temperatures, and a sunny day, providing a robust test of emissions detection, quantification, and overall performance of the system 100.

Figure 5B:
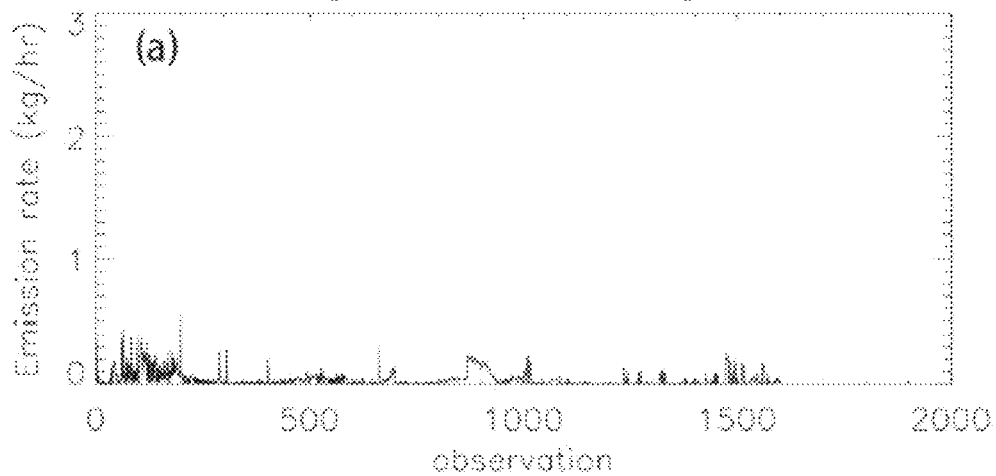
FIG. 5B is a graph of the emission rates that were measured by the gas leak detection system when gas was not released.
Figure 5C:
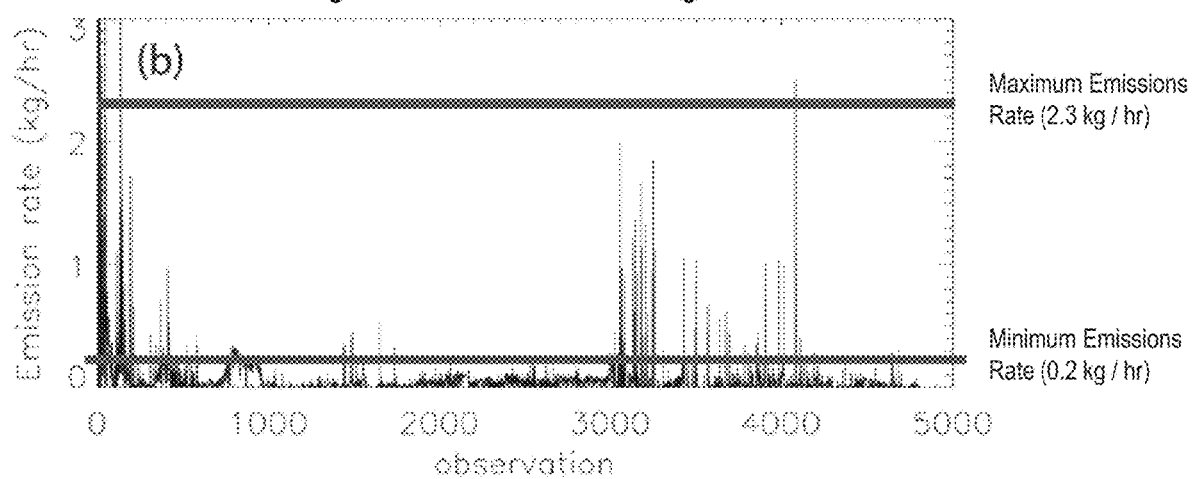
FIG. 5C is a graph of the emission rates that were measured by the gas leak detection system when gas was released.

FIG. 5B is a graph of the emission rates measured by all six sensor units 120 when METEC did not release gas. FIG. 5C is a graph of the emission rates measured by all six sensor units 120 when METEC released gas. METEC released methane at rates varying between 0.2 kg/hour and 2.3 kg/hour. FIGS. 5B and 5C show a clear difference in the measured emission rates when METEC released methane relative to when METEC did not release gas.

Figure 5D:
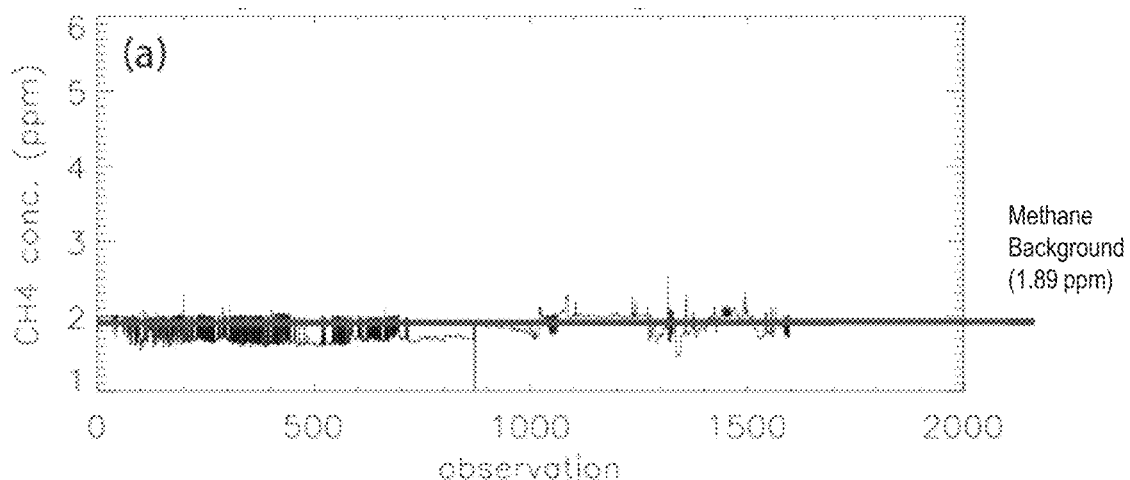
FIG. 5D is a graph of the methane concentration measured when gas was not released.
Figure 5E:
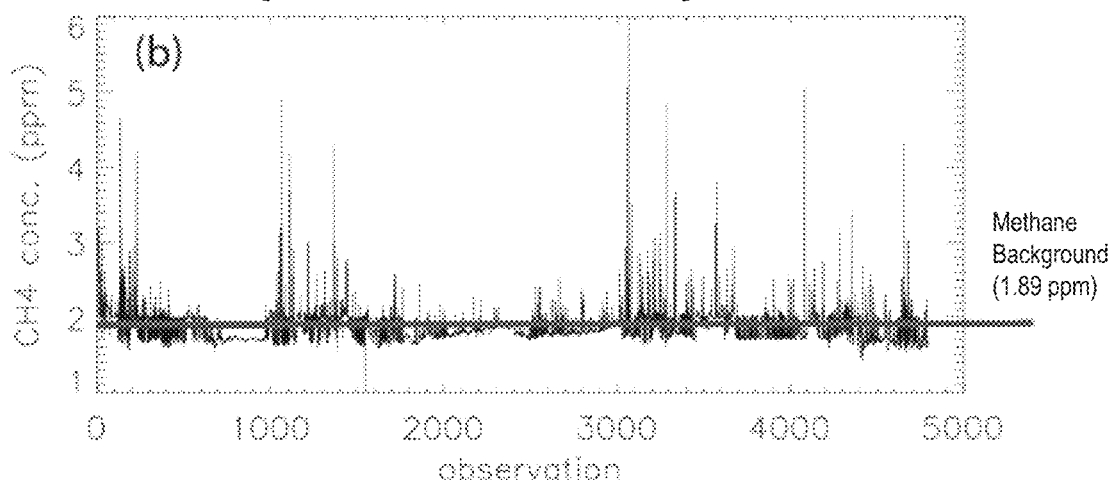
FIG. 5E is a graph of the methane concentration measured when gas was released.

FIG. 5D is a graph of the methane concentration measured by the gas leak detection system 100 when METEC did not release gas. FIG. 5E is a graph of the methane concentration measured by the gas leak detection system 100 when METEC released gas.

Figure 5F:
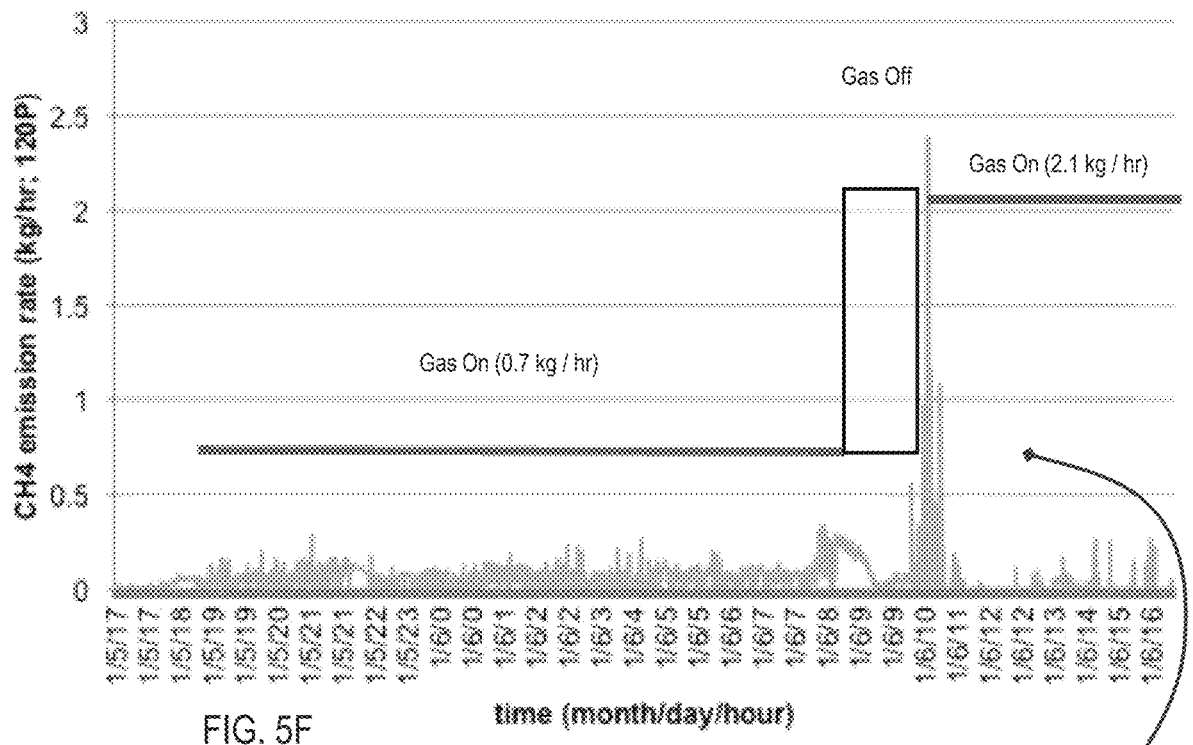
FIG. 5F is a graph of the emission rate measured by a first sensor unit during a selected time period of methane emissions testing and evaluation.
Figure 5G:
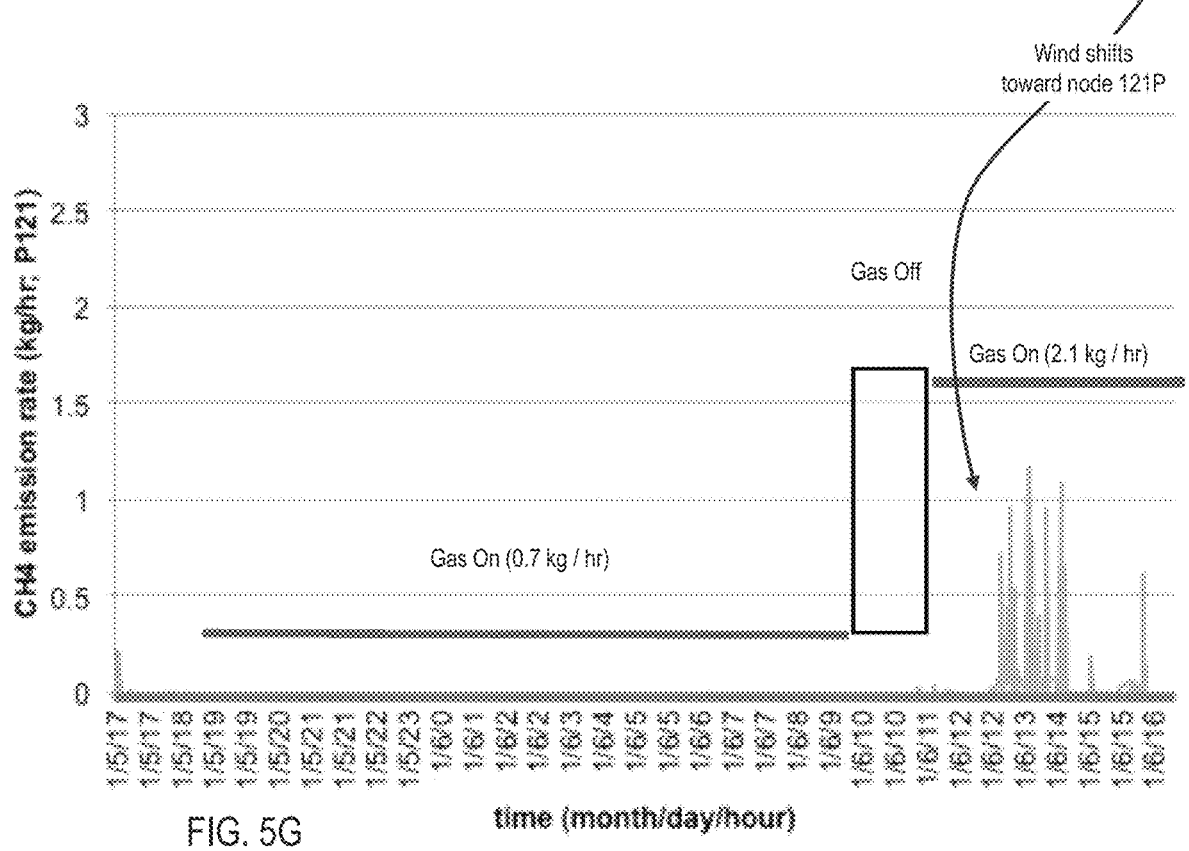
FIG. 5G is a graph of the emission rate measured by a second sensor unit during a selected time period of methane emissions testing and evaluation.

FIG. 5F is a graph of the emission rate measured by the primary sensor unit 120P during a selected time period. FIG. 5G is a graph of the emission rate measured by the primary sensor unit 121P during the selected time period. During the selected time period, METEC released gas at a rate of 0.7 kg/hour, stopped releasing gas, then released gas at a rate of 2.1 kg/hour. Winds favored measurements from node 120P (Northwest) and 121P (East). Both the primary sensor unit 120P and the primary sensor unit 121P were approximately 130 feet from the source 501.

A "difference of means" analysis was run on the entire time series of data to determine whether the calculated emissions rates for METEC were different for (1) METEC gas flow "gas off" versus "gas on" and (2) METEC gas flow at low rate (~0.6-1.2 kg/hour) vs. high rate (1.2-2.1 kg/hour). In both situations, the calculated emissions rates are significantly different at a 99% confidence level. Therefore, we can conclude that the gas leak detection system 100 found significant differences between when METEC was releasing gas or not. In other words, the gas leak detection system 100 detected the releases. And we can conclude that the gas leak detection system 100 was able to discriminate between periods of low gas release versus periods of high release.

The gas leak detection system 100 demonstrated the ability to detect fine changes in methane concentrations under field conditions, including the ability to account for changes in background air conditions. The results of the testing and evaluation suggest that the gas leak detection system 100 can detect a natural gas emission rate of at least 1.0 kg/hour at distances ranging from 130 to 180 feet from the source 501. In this test, the gas leak detection system 100 could detect a methane increase above background of at least 0.3 ppm. Finally, the full results of the testing and evaluation suggest that the gas leak detection system 100 can quantify emission rates with a reasonable accuracy in typical conditions. Given these results, the objective conclusion is that the gas leak detection system 100 excels as a continuous emissions monitoring platform, far exceeding minimum detections limits (MDL) set forth by the EPA (10 kg/hour MDL) and MiQ Certification (25 kg/hour as MDL).

Each sensor unit 120 may operate as a stand-alone sensing system that directly communicates with a user device (e.g., cell phone, desktop computer) via a custom application. However, the gas leak detection system 100 provides additional advantages when multiple sensor units 120 are used to model and determine emission rates across a site 10.

Gas Leak Emission and Dispersion Modeling

Measuring gas concentrations from a single location is insufficient to identify the likely source of a gas leak because the gas concentration at the location of a sensor also depends on the distance from the emission source to the sensor and the dispersion and mixing along that distance. Measuring gas concentration without also measuring influencing factors like wind conditions (or extrapolating atmospheric conditions from distant measurements or relatively low-resolution numerical forecast models) limits the ability to convert gas concentration measurements to emission rates and total emissions. And even highly sophisticated instruments that measure gas concentrations at impressive accuracies—but that do so at only a single location and/or infrequent time intervals—are only able to provide a crude range of possible emission rates for locations on a site 10.

As described above, the low cost sensor units 120 enable gas concentrations 590 to be measured at regular intervals from multiple locations at or near a site 10. Meanwhile, the sensor units 120 also measure atmospheric conditions (wind speed, wind direction, air temperature) at the site 10. Accordingly, as described below, the gas leak detection system 100 is able to model gas dispersion (in two- or three-dimensions) across the site 10 and identify the emissions rates at each point in that two- or three-dimensional space that when dispersed according to the model, match the gas concentrations 590 measured by the sensor units 120 at or near the site 10. By visualizing the emissions rates across the site 10, the gas leak detection system 100 helps pinpoint the likely source of the gas leak.

Figure 6:
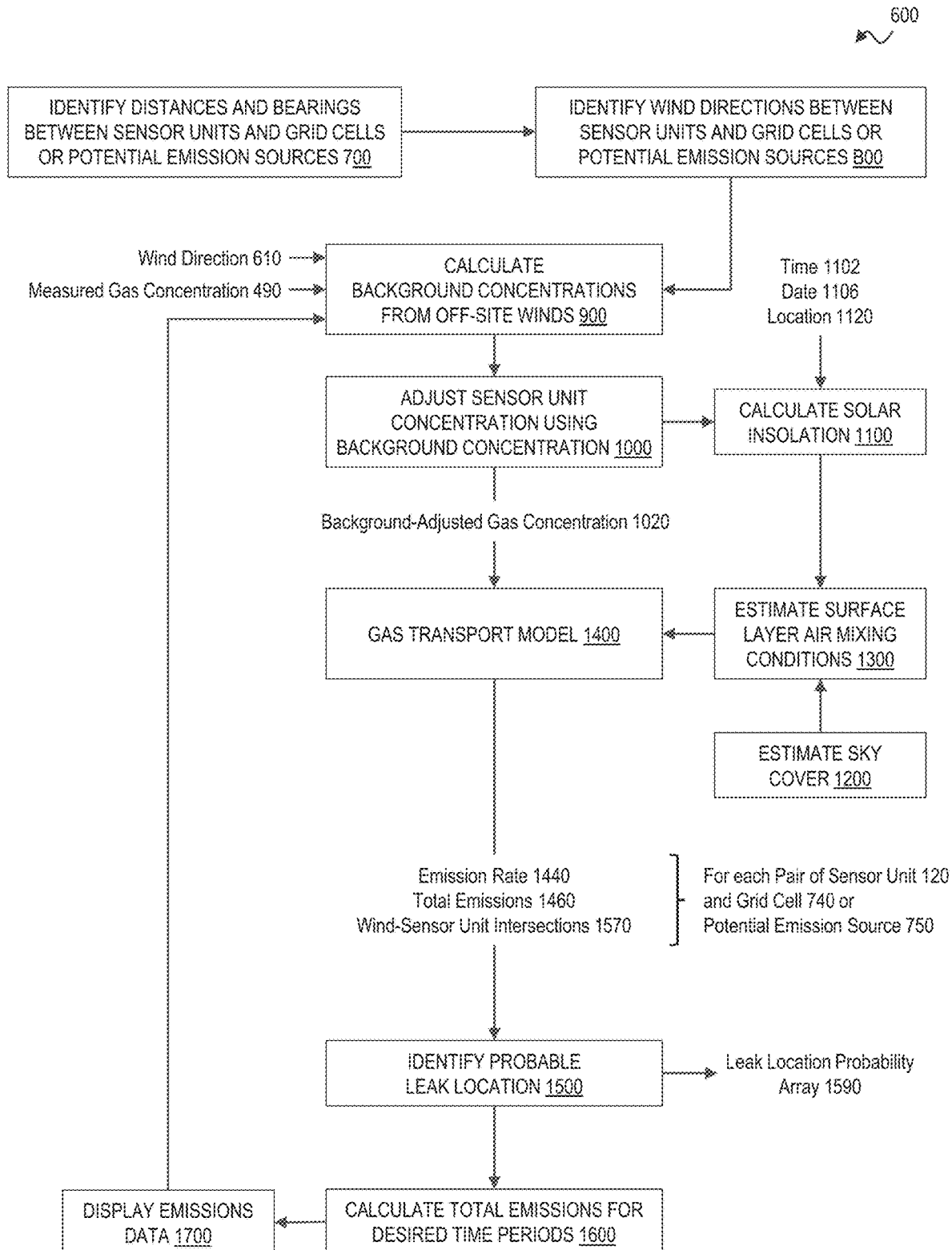
FIG. 6 is a flowchart of a gas leak mapping process according to an exemplary embodiment.

FIG. 6 is a flowchart illustrating a high-level overview of the gas leak emission and dispersion modeling process 600 according to an exemplary embodiment. The gas leak emission and dispersion modeling process 600 may be performed by the data analysis and reporting system 180, for example by receiving the data described below from the sensor units 120 (and, where applicable external sources 60), storing that data in the computer readable storage media 186, and performing the processing steps described below by the server 182.

At each site 10, a number of potential emission sources 740 (a well head 12, a separator 14, a storage tank 16, a pipeline, etc.) are identified or the site 10 is segmented into a number of (two- or three-dimensional) grid cells 730.

The gas leak emission and dispersion modeling process 600 begins with two pre-processing steps: In the process 700 (described below with reference to FIGS. 7A and 7B), the distances and bearings are identified between each sensor unit 120 and each grid cell 740 or potential emission source 750. Additionally, in the process 800 (described below with reference to FIGS. 8A and 8B), the wind directions are identified between each sensor unit 120 and each grid cell 740 or potential emission source 750.

Then, for each time step, the background concentrations from off-site winds are calculated in the process 900 (described below with reference to FIG. 9) and the measured gas concentration 490 received from the sensor unit 120 is adjusted to identify the background-adjusted gas concentration 1020 in the process 1000 (described below with reference to FIG. 10), and a gas transport model 1400 (e.g., an inverse Gaussian plume dispersion model) is used to calculate the emission rate 1440, the total emissions 1460, and the wind-sensor unit intersections 1570, for each pair of sensor unit 120 and grid cell 740 or potential emission source 750 in the process 1400 (as described below with reference to FIG. 14) based on the background-adjusted gas concentration 1020 and the wind direction 610 (determined, for example, by the anemometer 130 at the site 10). To do so, the solar insolation is calculated using the time 1102, the date 1106, and the location 1120 in the process 1100 (as described below with reference to FIG. 11), sky cover is estimated in the process 1200 (as described below with reference to FIG. 12), and the surface layer air mixing conditions are estimated in the process 1300 (as described below with reference to FIG. 13).

Figure 15A:
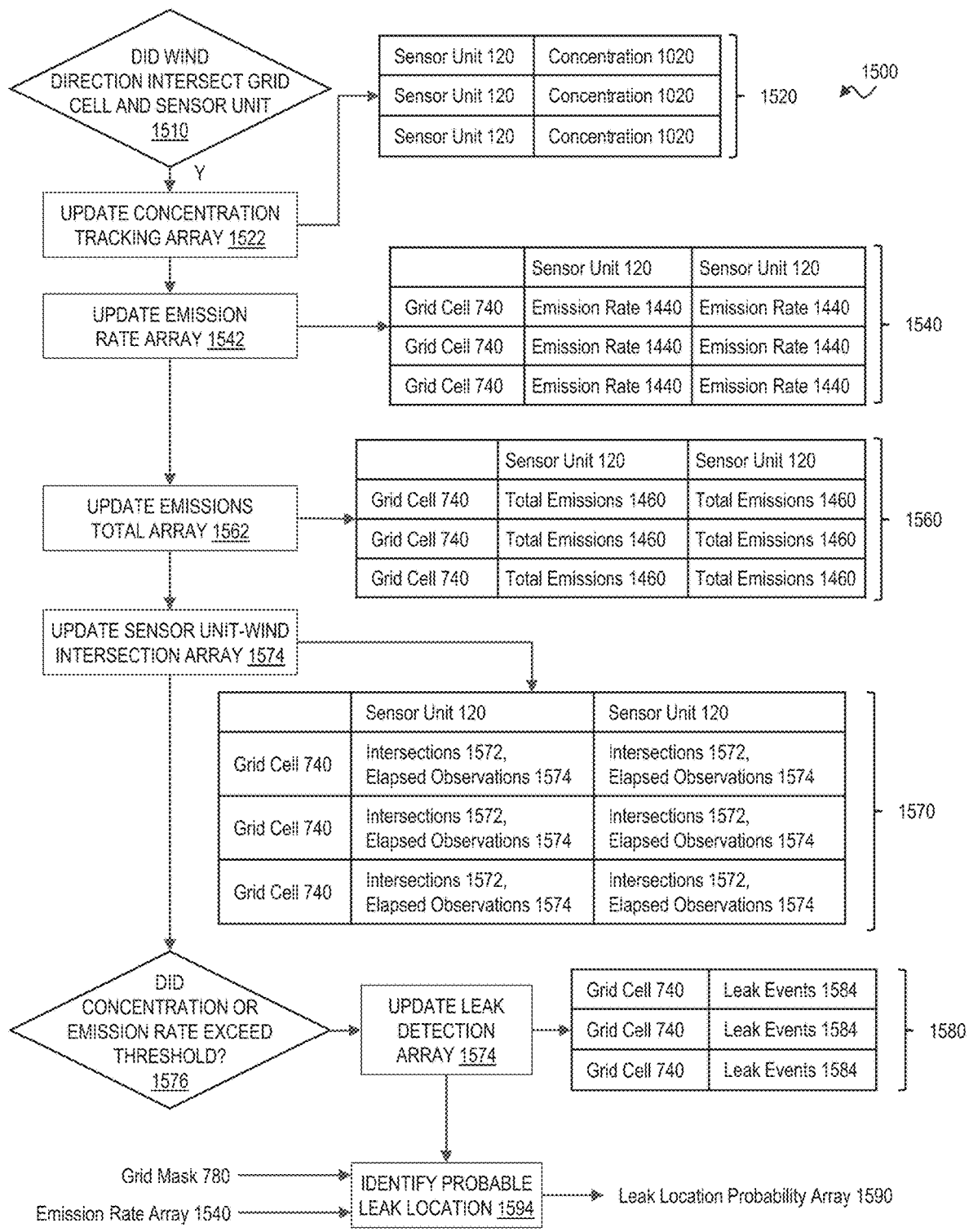
FIG. 15A is a flowchart illustrating a wind-cell intersection tracking array update process according to an exemplary embodiment.

A leak location probability array 1590 identifying the most probable leak location is generated in the process 1500 (as described below with reference to FIGS. 15A-C). Total emissions for desired time periods are calculated in the process 1600 (as described below with reference to FIG. 16). Emissions data and alerts are output in the process 1700 (as described below with reference to FIG. 17), for example via the dashboard 1800 (as described below with reference to FIGS. 18A through 18F).

Figure 7A:
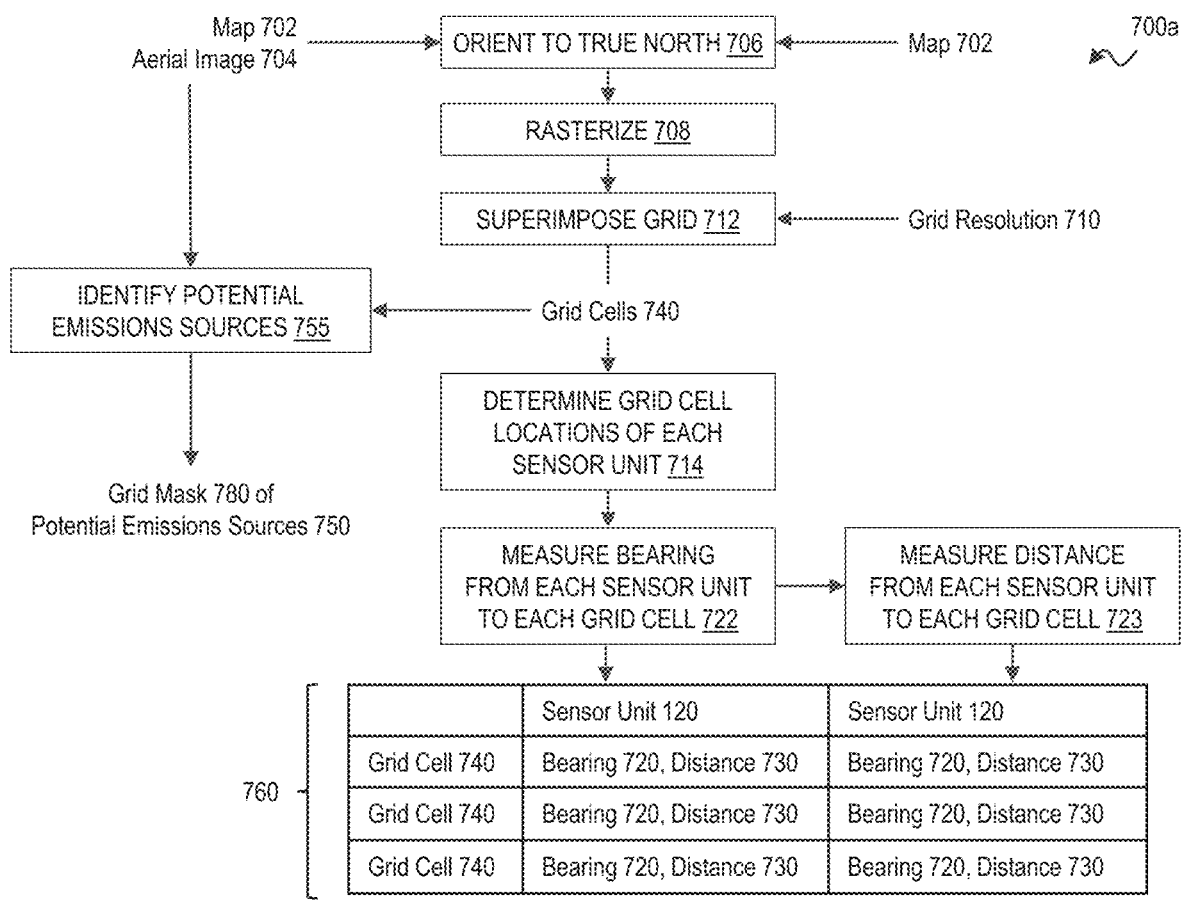
FIG. 7A is a flowchart of an automated distance and bearing identification process according to an exemplary embodiment.

FIG. 7A is a flowchart of an automated distance and bearing identification process 700*a* according to an exemplary embodiment. In the embodiment of FIG. 7A, bearings 720 and distances 730 between each sensor unit 120 and each grid cell 740 are identified and stored in a distance-bearing map 760. A map 702 or aerial image 704 of the site 10 is oriented to true north in step 706 and rasterized in step 708. A selected grid resolution 710 is received and a grid is superimposed over the map 702 or aerial image 704 to generate two- or three-dimensional grid cells 730 across the site 10 in in step 712. The grid cell locations of each sensor unit 120 are identified in step 714. The bearing 720 from each sensor unit 120 to each grid cell 740 is measured in step 722 and the distance 730 between each sensor unit 120 and each grid cell 740 is measured in step 723.

Additionally, a grid mask 780 is generated indicating the grid cells 740 that include a potential emissions source 750 (e.g., a well head 12, a separator 14, a storage tank 16, a pipeline, etc.) in step 755. The grid mask 780 may be manually generated. Alternatively, the grid mask 780 may be generated by using an object detection algorithm to identify potential emissions sources 750 in the aerial image 704 of the site 10. In embodiments where the grid cells 740 are three dimensional, potential emissions sources 750 may be modeled in three-dimensions (e.g., with the potential emissions source 750 being located at the top of a structure where a leak is most likely to occur).

Figure 7B:
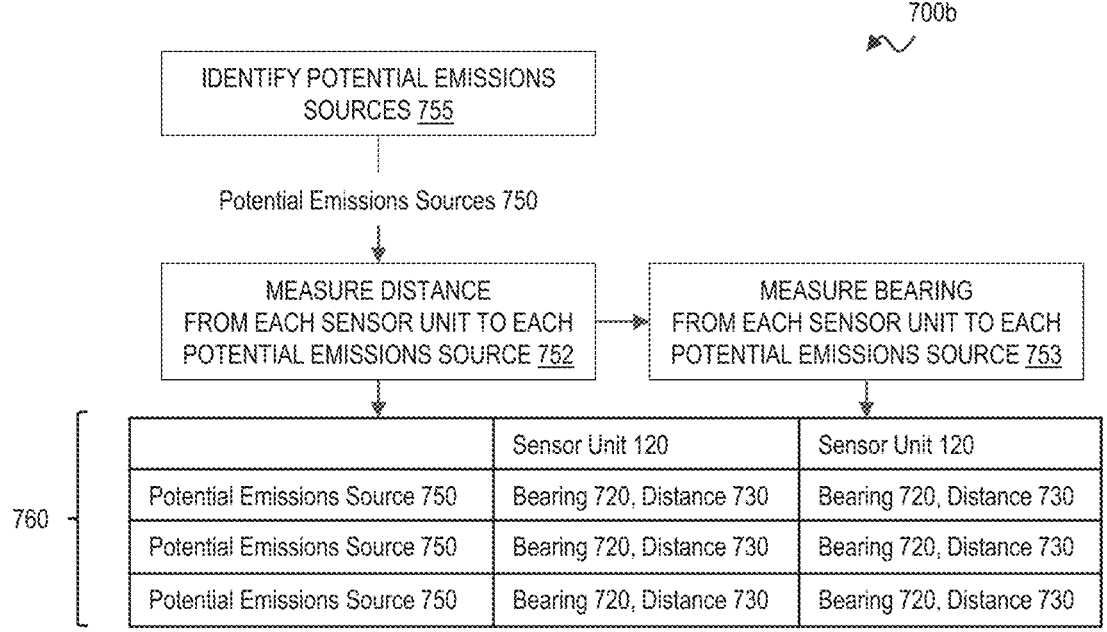
FIG. 7B is a flowchart of a manual distance and bearing identification process according to an exemplary embodiment.

FIG. 7B is a flowchart of a manual distance and bearing identification process 700*b* according to an exemplary embodiment. In some embodiments, a site 10 may include a limited number of sensor units 120 and a limited number of potential emissions sources 750. In those embodiments, the distance-bearing map 760 can be manually generated by identifying the potential emissions sources 750 in step 755, measuring the bearing 720 from each sensor unit 120 to each potential emissions source 750 in step 752, and measuring the distance 730 from each sensor unit 120 to each potential emissions source 750 in step 753.

Figure 8A:
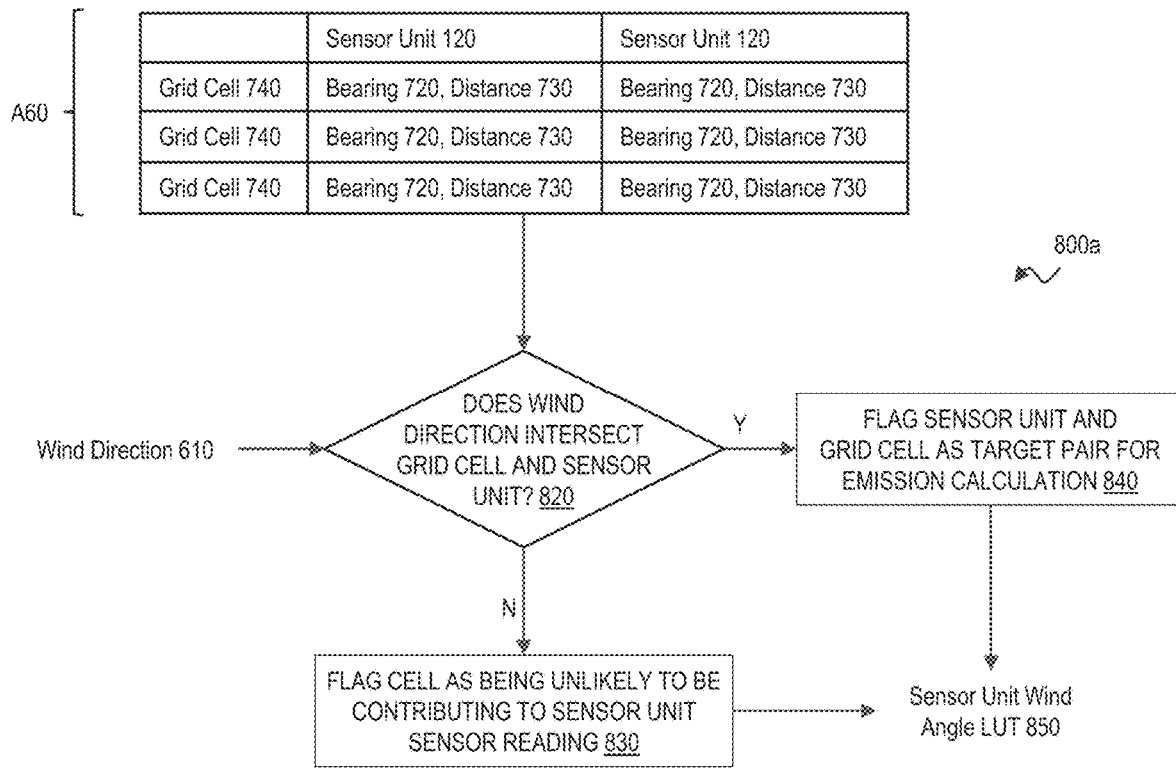
FIG. 8A is a flowchart of an automated wind direction identification process according to an exemplary embodiment.

FIG. 8A is a flowchart of an automated wind direction identification process 800*a* according to an exemplary embodiment. In the embodiment of FIG. 8A, for each potential wind direction 610, a determination is made in step 820 as to whether the wind direction 610 intersects with a grid cell 740 and a sensor unit 120. If not (step 820: No), that cell is flagged in step 830 as being likely to be contributing to the sensor reading of the sensor unit 120. If so (step 820: Yes), the sensor unit 120 and grid cell 740 pair is flagged as being a target pair for emission calculation in step 840. Those flags are stored in a sensor unit wind angle look-up table 850.

Figure 8B:
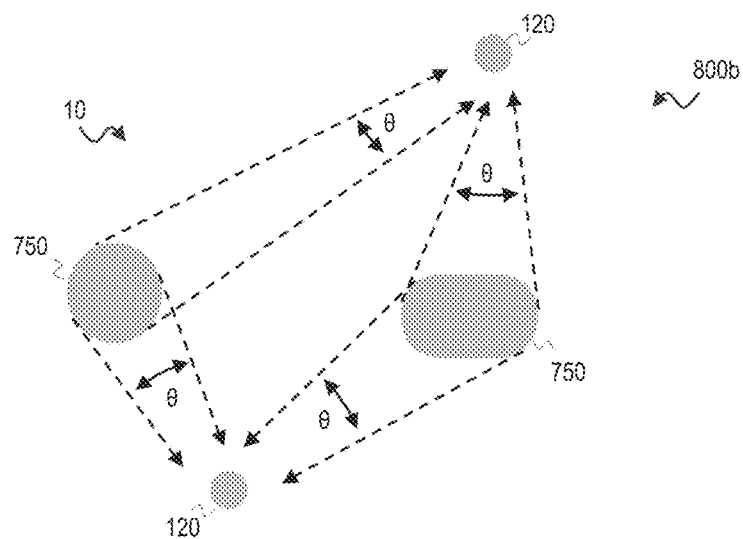
FIG. 8B is a diagram of a manual wind direction identification process 800b according to an exemplary embodiment.

FIG. 8B is a diagram of a manual wind direction identification process 800*b* according to an exemplary embodiment. In the embodiments described above with a limited number of sensor units 120 and a limited number of potential emissions sources 750, the wind directions θ intersecting each potential emissions source 750 and each sensor units 120 can be manually identified and stored in the wind angle look-up table 850.

Figure 9:
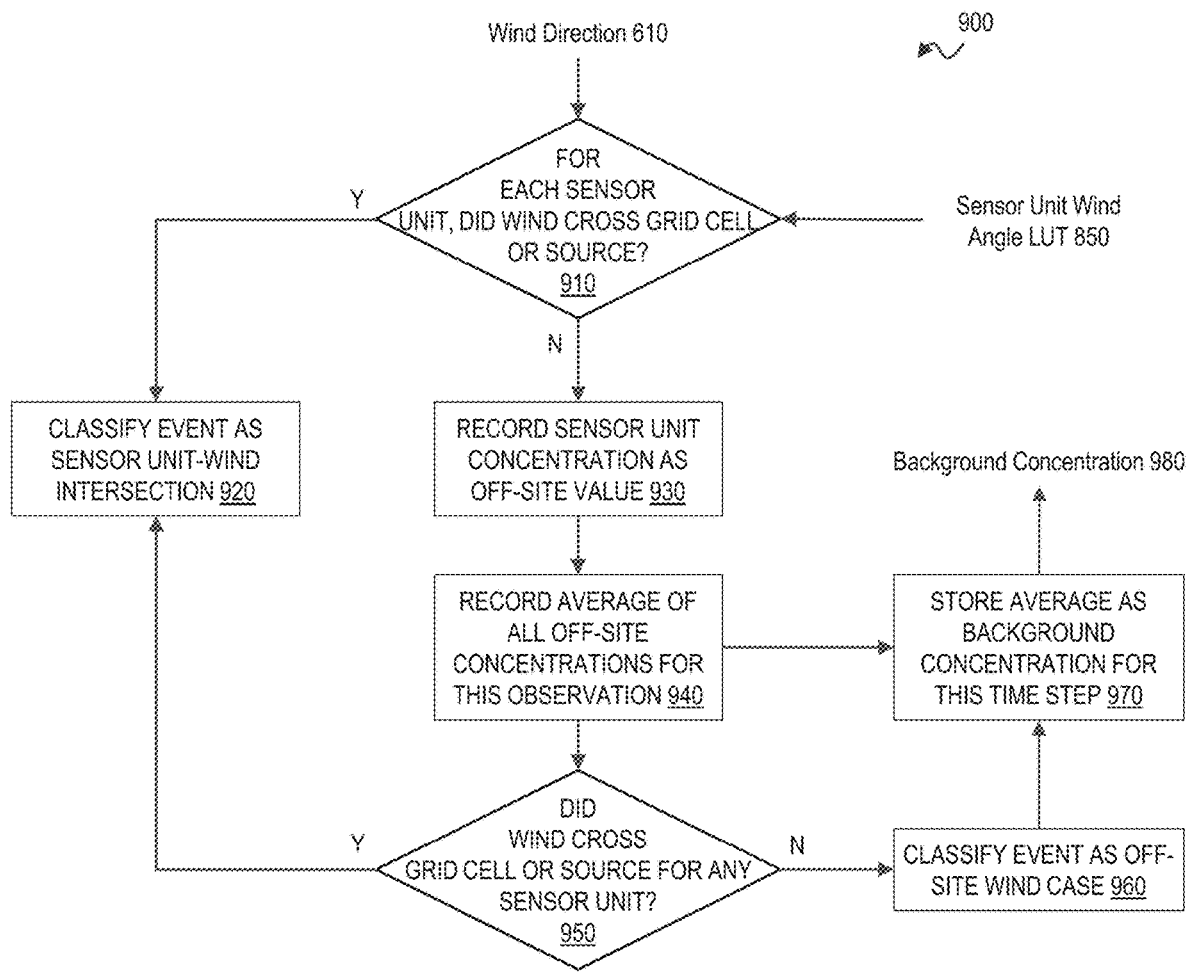
FIG. 9 is a flowchart illustrating a background concentration calculation process according to an exemplary embodiment.

FIG. 9 is a flowchart illustrating a background concentration calculation process 900 according to an exemplary embodiment. In the embodiment of FIG. 9, for the current wind direction 610, a determination is made in step 910 (using the sensor unit wind angle look-up table 850) as to whether the wind crossed a grid cell 740 or potential emissions source 750 and the sensor unit 120. If so (Step 910: Yes), the event is classified as a sensor unit-wind intersection in step 920. If not (Step 910: No), the measured concentration 530 is recorded as an off-site value in step 930 and the average of all off-site concentrations are recorded in step 940. If, in step 950, a determination is made that the wind did not cross any grid cell 740 or potential emissions source 750 for any sensor unit 120, the event is classified as an off-site wind case in step 960. The average background concentration 780 is stored in step 970.

Figure 10:
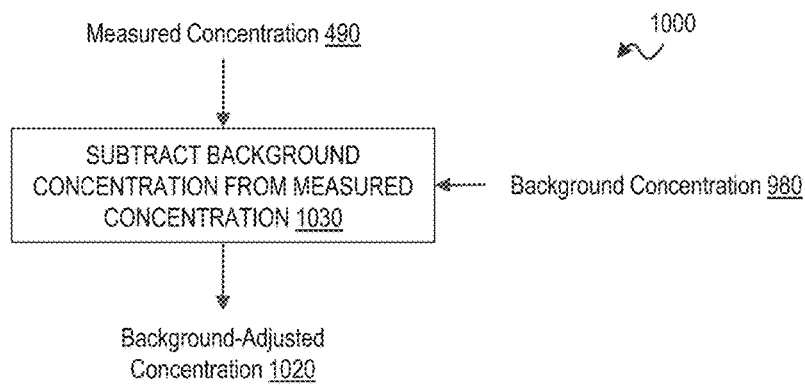
FIG. 10 is a flowchart illustrating a background concentration adjustment process according to an exemplary embodiment.

FIG. 10 is a flowchart illustrating a background concentration adjustment process 1000 according to an exemplary embodiment. In the embodiment of FIG. 10, the background concentration 780 for each time step is subtracted from the measured concentration 490 for that time step to form the background-adjusted concentration 1020 in step 1030.

Figure 11:
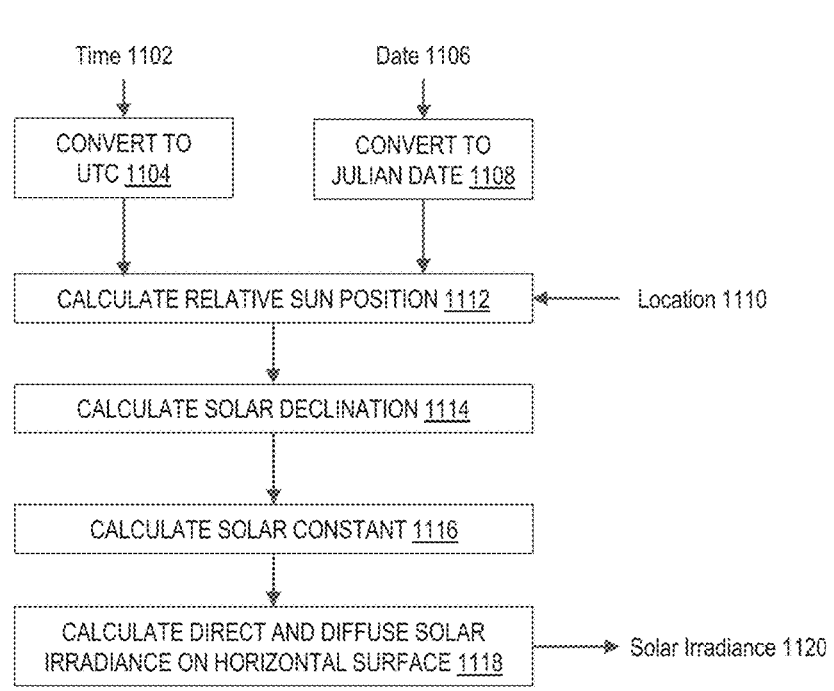
FIG. 11 is a flowchart illustrating an example solar irradiance calculation process.

FIG. 11 is a flowchart illustrating an example solar irradiance calculation process 1100 for calculating solar irradiance 1120. As shown in FIG. 11, the time 1102 is converted to UTC in step 1104, the date 1106 is converted to the Julian date in step 1108, and (using the location 1110) the relative sun position is calculated in step 1112, the solar declination is calculated in step 1114, the solar constant is calculated in step 1116, and the direct and diffuse solar irradiance 1120 is calculated in step 1118.

Figure 12:
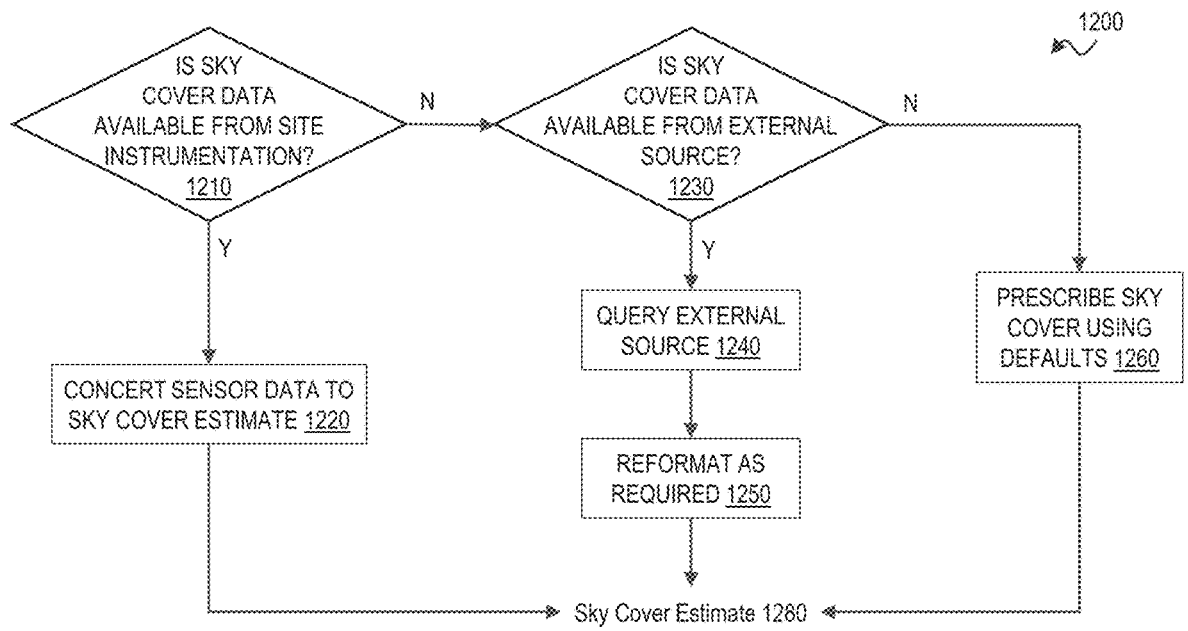
FIG. 12 is a flowchart illustrating a sky cover estimation process according to an exemplary embodiment.

FIG. 12 is a flowchart illustrating a sky cover estimation process 1200 according to an exemplary embodiment. In the embodiment of FIG. 12, if sky cover data is available from the instrumentation at the site 10 (step 1210: Yes), that sensor data is converted to a sky cover estimate 1280 in step

1220. If sky cover data is not available from the instrumentation at the site 10 (step 1210: No), a determination is made in step 1230 as to whether sky cover data is available from an external source 60 (e.g., the National Environmental Satellite Data and Information Service, Solcast, the nearest National Weather Service Automated Surface Observation System, etc.). If so (step 1230: Yes), the external source 60 is queried in step 1240 and reformatted in step 1250 to form the sky cover estimate 1280. If sky cover data is not available from the instrumentation at the site 10 (step 1210: No) or an external source 60 (step 1230: No), a default sky cover estimate is identified in step 1260 and used as the sky cover estimate 1280.

Figure 13:
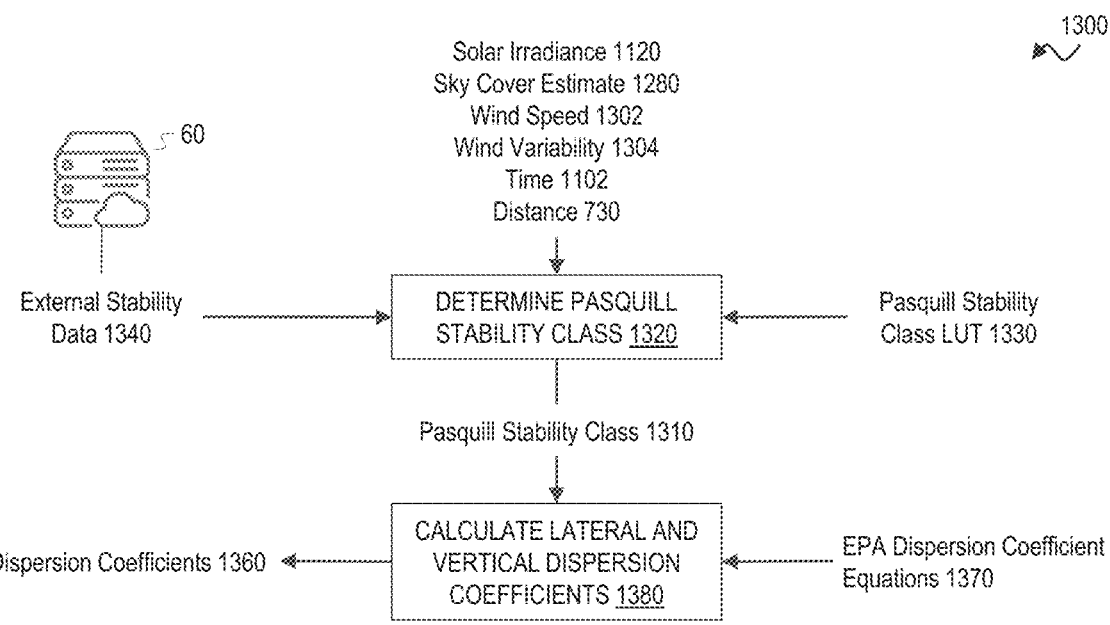
FIG. 13 is a flowchart illustrating a surface layer air mixing conditions estimation process according to an exemplary embodiment.

FIG. 13 is a flowchart illustrating a surface layer air mixing conditions estimation process 1300 according to an exemplary embodiment. In the embodiment of FIG. 13, the Pasqill stability class 1310 is determined in step 1320 using a Pasquill stability class look-up table 1330 adapted from published literature and the solar irradiance 1120 (determined as described above with reference to FIG. 11), the sky cover estimate 1280 (determined as described above with reference to FIG. 12), the wind speed 1302 (determined, for example, by the anemometer 130 at the site 10), the wind variability 1304 (determined based on variance in the wind speed 1302 and wind direction 610 measurements over time, an external weather data source, etc.), the time 1102 of day, and the distance 730 from the sensor unit 120 to the grid cell 740 or the potential emissions source 750. External stability data 1340 from external sources 60, such as the U.S. Environmental Protection Agency (EPA) rawindsonde observations from online sources (e.g., University of Wyoming soundings database for North America), or estimations from forecast model output may also be used to identify the Pasquil stability class 1310. Lateral and vertical dispersion coefficients 1360 are calculated using the Pasquill stability class 1310 and dispersion coefficient equations 1370 generated by calculating regression fits for data in tables of lateral and vertical dispersion parameters published by EPA in step 1380. In situations of very light winds (under 1.1 m/s) and/or stable surface layer conditions, the dispersion coefficients 1360 may be modified to account for added lateral mixing due to meandering.

Figure 14:
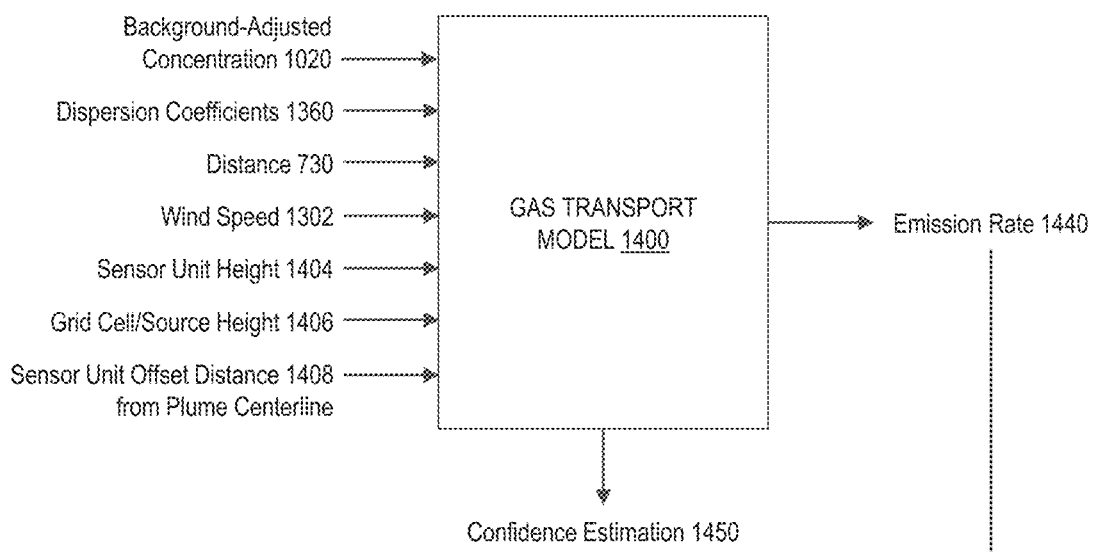
FIG. 14 is a flowchart illustrating a gas transport model according to an exemplary embodiment.

FIG. 14 is a flowchart illustrating a gas transport model 1400 according to an exemplary embodiment. In the embodiment of FIG. 14, the gas transport model 1400 (e.g., an inverse Gaussian plume dispersion model) models the dispersion at the site 10 using the dispersion coefficients 1360 and other data and identifies the emission rate 1440 at the selected grid cell 740 or potential emission source 750 that would be most likely to cause the background-adjust concentration 1020 at the selected sensor unit 120. To model the dispersion at the site 10, the gas transport model 1400 may also be provided with the distance 730 from the sensor unit 120 to the grid cell 740 or the potential emissions source 750, the wind speed 1302 (determined, for example, by the anemometer 130 at the site 10), the sensor unit height 1404 (e.g., the height 1404 of the opening of the intake port 122 or intake tube 123), and the height 1406 of the potential emissions source 750 or object on the grid cell 740. The system 100 also specifies an offset distance 1408 from the sensor unit 120 to the plume centerline. For example, the plume centerline may be assumed to align with the sensor unit 120 and the grid cell 740 (i.e., an offset distance 1408 of zero). However, the calculations may be performed with different assumed offset distances 1408, for to provide a range of potential emission rates 1440 per observation or if wind direction 610 is known to a fine angle resolution. In some embodiments, additional data may be provided to and used by the gas transport model 1400. For example, in the embodiments described above where the sensor unit 120 includes two intake tubes 123 to collect air samples from two different heights, the observed temperature 442 at both heights may be provided to help the gas transport model 1400 define the vertical stability of the atmosphere (a key parameter defining the prescribed vertical and lateral mixing of a plume) and the shape of the concentration distribution in the vertical dimension (a key element of, for example, a Gaussian plume model).

The gas transport model 1400 may be a Gaussian plume model. Additionally, for calm, stable conditions, a lateral diffusion model may be used in place of the wind-driven Gaussian plume dispersion model.

To calculate the total emissions 1460 for the selected time step, the emission rate 1440 is multiplied by the duration 1462 of the time step in step 1466. The gas transport model 1400 may also identify a confidence estimation 1450 for the emission rate 1440 identified and the gas transport model 1400 may flag any calculated emission rate 1400 as having a particularly high or low confidence estimation 1450 if that confidence estimation 1450 meets or exceeds predetermined confidence threshold.

FIG. 15 illustrates a wind-cell intersection tracking array update process 1500 according to an exemplary embodiment. In the embodiment of FIG. 15, the gas leak detection system 100 stores a concentration tracking array 1520 that includes the background-adjusted concentrations 1020 measured by each sensor unit 120, an emission rate array 1540 that includes the emission rates 1440 calculated by the gas transport model 1400 for each pair of sensor unit 120 and grid cell 740 (or potential emissions source 750), an emissions total array 1560 that includes the total emissions 1460 for each pair of sensor unit 120 and grid cell 740 (or potential emissions source 750), a wind-unit intersection array 1570 that includes the number of intersections 1572 when the wind direction 610 intersected each sensor unit 120 and grid cell 740 (or potential emissions source 750), information indicative of the intersections each sensor unit 120 and each grid cell 740 (or potential emissions source 750) for each observations, the number of elapsed observations 1574 since the wind direction 610 intersected each sensor unit 120 and each grid cell 740 (or potential emissions source 750). The aforementioned arrays hold a variety of information valuable for assessing how well the sensor units 120 are sampling the site (a function primarily of placement of the sensor units 120 relative to prevailing wind directions 610), which sensor units 120 tend to observe the highest gas concentrations 1020, and which combinations of sensor units 120 and grid cell 740 (or potential emissions source 750) are linked most often by wind patterns.

In the embodiment of FIG. 15, if the wind direction 610 intersects a sensor unit 120 and grid cell (or potential emissions source 750) in step 1510, the concentration tracking array 1520 is updated in step 1522, the emission rate array 1540 is updated in step 1542, the emissions totals array 1560 is updated in step 1562, and the sensor unit-wind intersection array 1572 is updated in step 1574.

If the background-adjusted concentration 1020 or emission rate 1440 meets or exceeds a predetermined threshold in step 1576, a leak detection tracking array 1580, which includes the number of leak events 1584 in each grid cell 740 or at each potential emission source 750 meeting or exceeding that predetermined threshold, is updated in step 1582. Additionally, a leak location probability array 1594 identifying the most probable leak location is identified in step 1594.

Figure 15B:
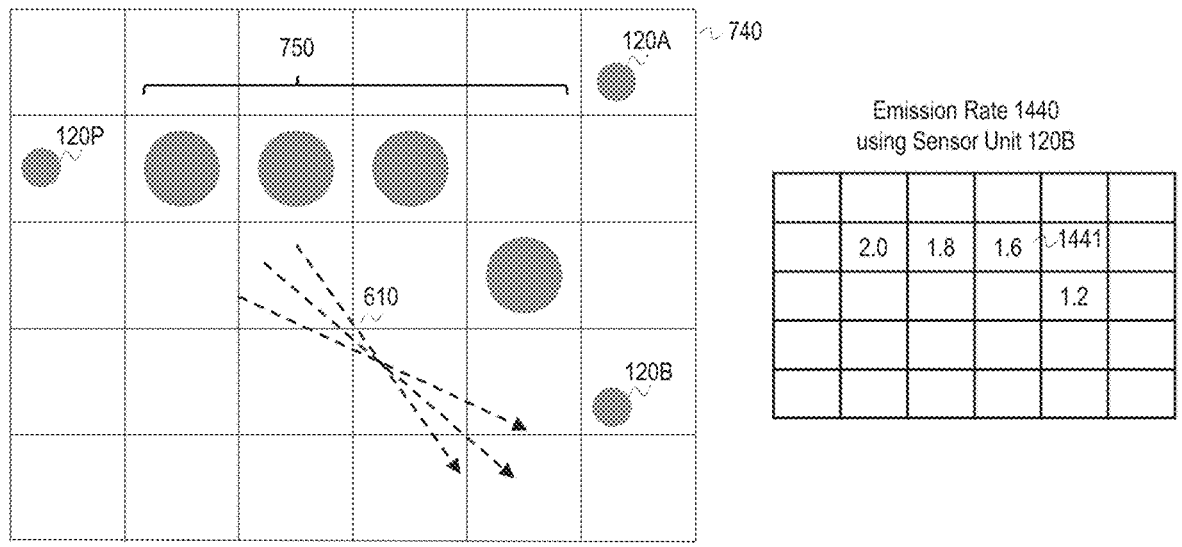
FIG. 15B is a diagram illustrating a process for identifying the most probable leak location according to an exemplary embodiment.
Figure 15C:
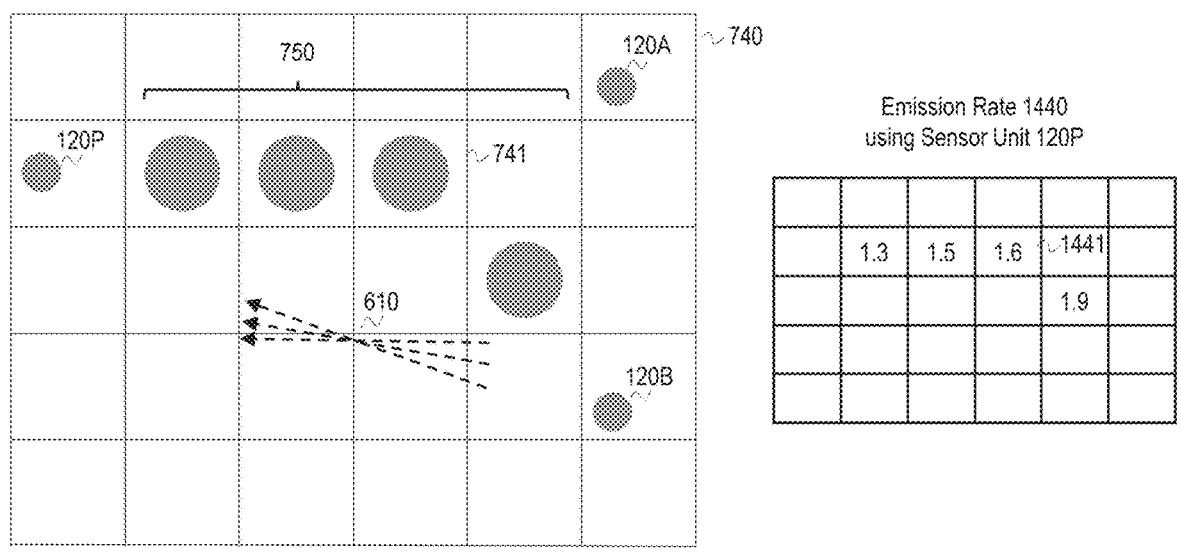
FIG. 15C is a diagram illustrating a subsequent step in the process for identifying the most probable leak location according to an exemplary embodiment.

FIGS. 15B and 15C illustrate the process 1594 for identifying the most probable leak location according to an exemplary embodiment. In the example of FIG. 15B, the site 10 includes a number of sensor units 120 and a number of potential emissions sources 750 in a number of grid cells 740. Over a first time period, the wind direction 610 generally faces the sensor unit 120B, leading the sensor unit 120B to measure a higher concentrations 1020 than sensor units 120P and 120A. At each time step, the gas transport model 1400 estimates the emissions rate 1440 in each grid cell 740 that would result in the concentration 1020 measured by the sensor unit 120B. (Using the grid mask 780 of potential emissions sources 750 described above, the system 100 may be configured to only calculate the emissions rates 1440 in grid cells 740 that include a potential emissions source.)

As shown in FIG. 15C, the wind direction 610 generally faces the sensor unit 120B, leading the sensor unit 120P to measure a higher concentrations 1020 than sensor units 120A and 120B. Again, the gas transport model 1400 estimates the emissions rate 1440 in each grid cell 740 that would result in the concentration 1020 measured by the sensor unit 120P. To identify the likely emitter source, the system 100 takes advantage of the fact that the calculated emissions rate 1440 at a given grid cell 740 should be similar when calculated using data from different sensor units 120. More specifically, the probability that each grid cell 740 includes the emitter source is inversely proportional to the variance between the emissions rates 1440 for that grid cell 740 calculated using the concentration 1020 measured by two different sensor units 120. In the example of FIGS. 15B and 15C, for instance, the likely emitter source is in grid cell 741, where the system 100 estimated the same emissions rate 1441 (in this example, 1.6) using the concentration 1020 measured by sensor units 120B and 120P.

Referring back to FIG. 15A, the leak location probability array 1590 is generated by calculating the variance between the emissions rates 1440 for each grid cell 740 measured using sensor data 300 from two different sensor units 120.

Figure 16:
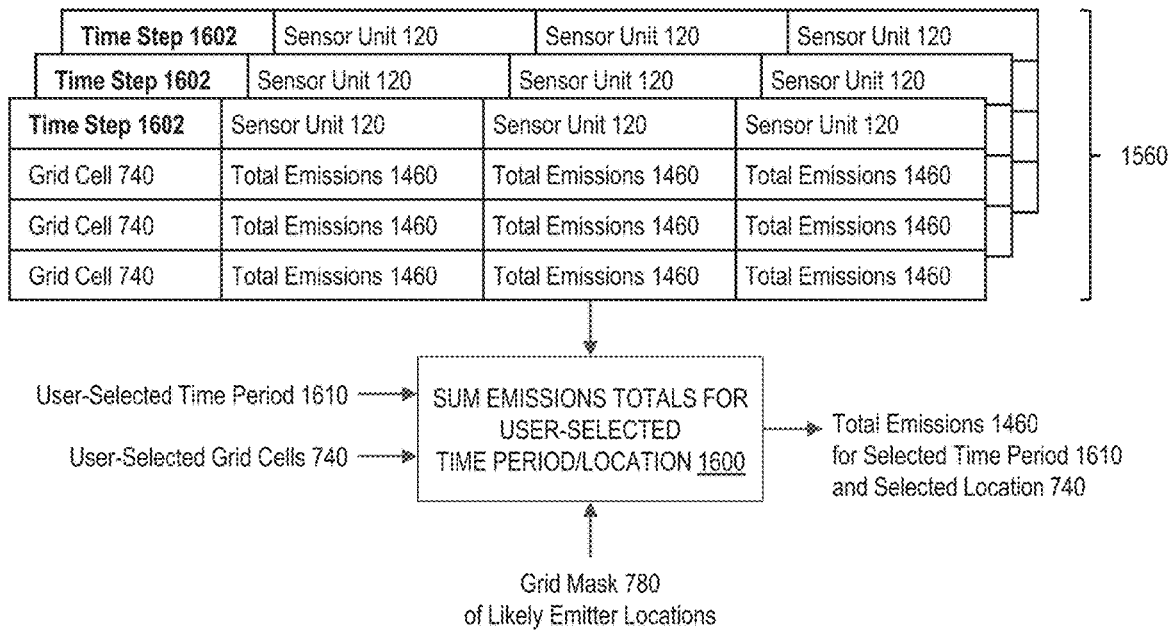
FIG. 16 is a flowchart illustrating a process for calculating the total emissions for a user-selected time period and user-selected location according to an exemplary embodiment.

FIG. 16 is a flowchart illustrating a process 1600 for calculating the total emissions 1460 for a user-selected time period 1610 and user-selected location (i.e., grid cells 740 or potential leak source 750) according to an exemplary embodiment. As described above, the emissions totals array 1560 includes the total emissions 1460 for each pair of sensor unit 120 and grid cell 740 (or potential emissions source 750) for each time step 1602. Accordingly, the total emissions 1460 for a user-selected time period 1610 and a user-selected location can be calculated by summing the total emissions 1460 identified by each sensor unit 120 for each grid cell 740 (or potential emissions source 750) specified by the user and each time step 1602 in the time period 1610 specified by the user. The grid mask 780 is applied to limit the calculation of total emissions to only those grid cells 740 that include probable emissions sources 750.

Figure 17:
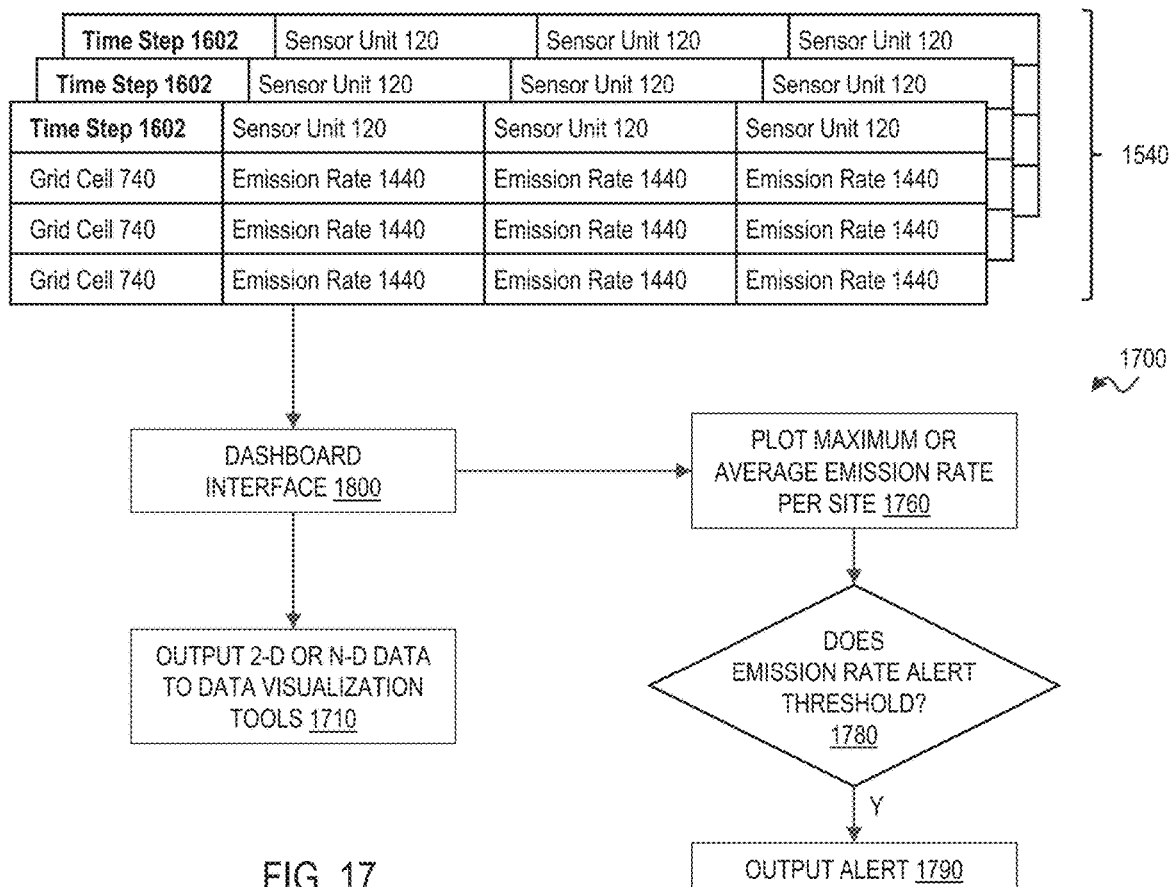
FIG. 17 is a flowchart illustrating an emissions data output process according to an exemplary embodiment.

FIG. 17 is a flowchart illustrating an emissions data output process 1700 according to an exemplary embodiment.

As described above, the emission rate array 1540 includes the emission rate 1440 for each pair of sensor unit 120 and grid cell 740 (or potential emissions source 750) for each time step 1602. Accordingly, that data can be output to the user via a dashboard interface 1800 (described below with reference to FIGS. 18A through 18F) that includes two-dimensional and/or n-dimensional data visualization tools 1710. Additionally, in the embodiment of FIG. 17, the maximum or average emission rate 1440 for the site 10 is plotted in step 1760. and, if the plotted emission rate 1440 meets or exceeds a predetermined alert threshold in step 1780, an alert is output in step 1790 (e.g., via email, text message, and/or the dashboard interface 1800) to a party responsible for monitoring the site 10. As noted above, the grid mask 780 is used to limit some calculations (such as emissions totals and average concentrations) to those cells known to be potential emission sources. However, these masking steps may be done at the end of the processing and data presentation. It is therefore possible to search for potential unknown locations of emissions, or to include those locations later if new site information becomes available.

Dashboard and Alerts

Figure 18A:
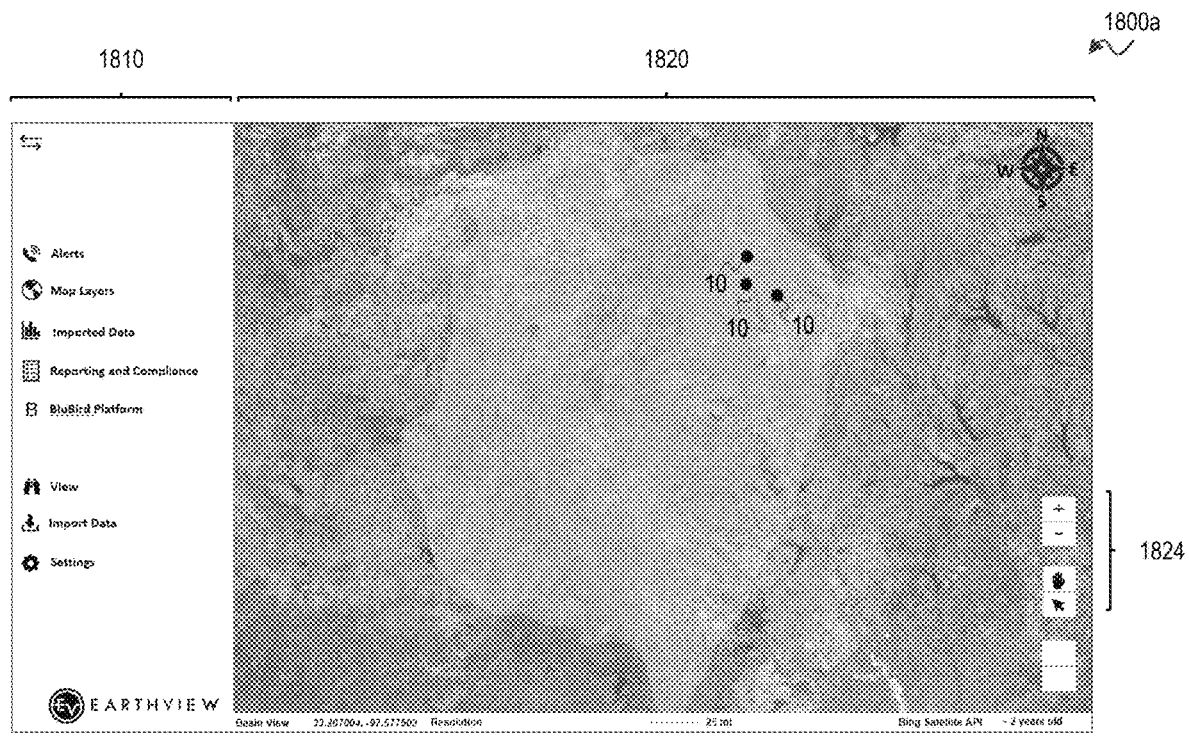
FIG. 18A is a view of the dashboard interface according to an exemplary embodiment.

FIG. 18A is a view 1800a of the dashboard interface 1800 according to an exemplary embodiment. In the embodiment of FIG. 18A, the dashboard interface 1800 includes a menu 1810 and a map view 1820 (with map controls 1824) that enables users to view the locations of each site 10.

Figure 18B:
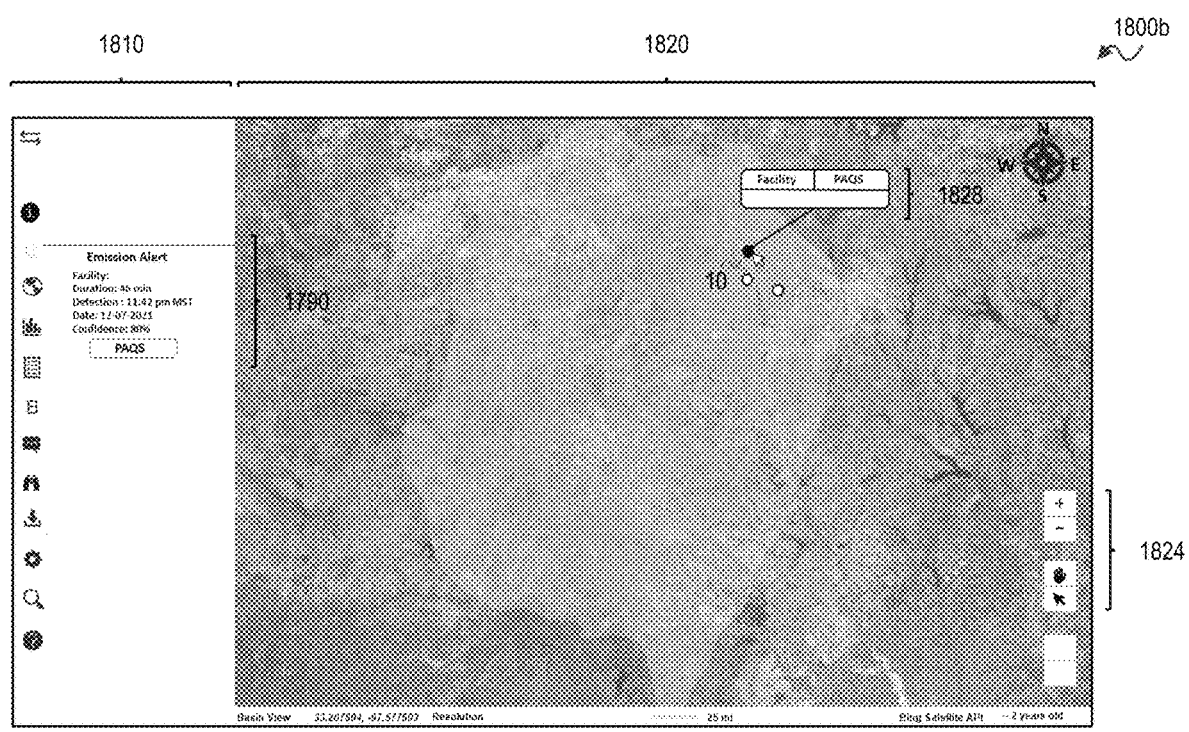
FIG. 18B is another view of the dashboard interface according to an exemplary embodiment.

FIG. 18B is a view 1800b of the dashboard interface 1800 according to an exemplary embodiment. In the embodiment of FIG. 18B, the dashboard interface 1800 includes an alert 1790 regarding a site 10, including a confidence rate 1450 that an emissions rate 1440 at the site 10 meets or exceeds the predetermined alert threshold. The dashboard interface 1800 also provides functionality 1828 to view the emission rates 1440 for each grid cell 740 (or potential emissions source 750) at the site 10 using the two-dimensional (or n-dimensional) data visualization tools 1710, for example as described below.

Figure 18C:
FIG. 18C is another view of the dashboard interface according to an exemplary embodiment.

FIG. 18C is a view 1800c of the dashboard interface 1800 according to an exemplary embodiment. In the embodiment of FIG. 18C, the map area 1820 includes the map 702 or aerial image 704 of the site 10.

Figure 18D:
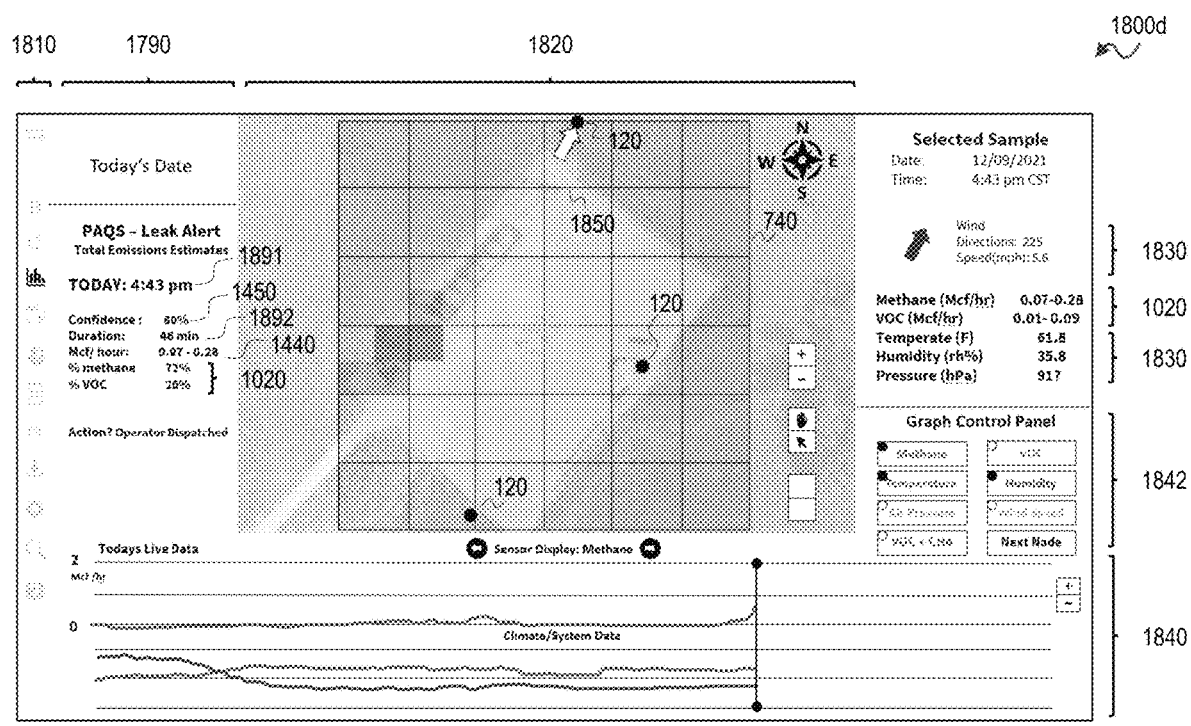
FIG. 18D is another view of the dashboard interface according to an exemplary embodiment.

FIG. 18D is a view 1800d of the dashboard interface 1800 according to an exemplary embodiment. In the embodiment of FIG. 18D, the view 1800d includes the alert 1790 and a map area 1820. The alert 1790 includes the time 1891 of the potential leak event, the emissions rate 1440 during the leak event, the confidence rate 1450 identified by the gas transport model 1400 that an emissions rate 1440 meets or exceeds the predetermined alert threshold, the duration 1892 of the leak event, and the background-adjusted concentrations 1020 (e.g., the relative concentrations of methane and volatile organic compounds).

The map area 1820 includes grid cells 740 across the site 10 and the locations of the sensor units 180 at the site 10. To visually indicate the locations of likely emissions sources at the site 10, the grid cells 740 that include a potential emissions source 750 (as determined by the grid mask 780) are color coded (e.g., grid cell 1850 of FIG. 18D) based on the emission rate 1440 or total missions 1460 at each grid cell 740. For example, grid cells 740 with increasing higher emission rates 1440 or total emissions 1460 may be blue, yellow, and red. Additionally, the transparency of the color may be proportional to the emission rates 1440 or total emissions 1460. Accordingly, as shown in FIG. 18D, the data visualization of the gas leak detection system 100 allows the user to virtually walk through the emissions plumes at the site 10, providing a powerful tool for identifying the most likely leak sources on a site 10.

For each selected sample, the view 1800d also includes the background-adjusted gas concentration 1020 (e.g., the measured concentration of methane and volatile organic compounds) as well as the environmental conditions 1830 (e.g., the air temperature 412, the relative humidity 414, the specific humidity 416, the atmospheric pressure, the wind speed 1302, the wind direction 610, etc.). The view 1800*d* also includes a graph area 1840 that displays the plotted background-adjusted gas concentrations 1020 for a user selected gas (e.g., methane, volatile organic compounds, etc.) or environmental condition 1830 (e.g., temperature (e.g., the air temperature 412, the relative humidity 414, the specific humidity 416, the atmospheric pressure, the wind speed 1302, the wind direction 610, etc.) selected, for example, using the graph control panel 1842.

Figure 18E:
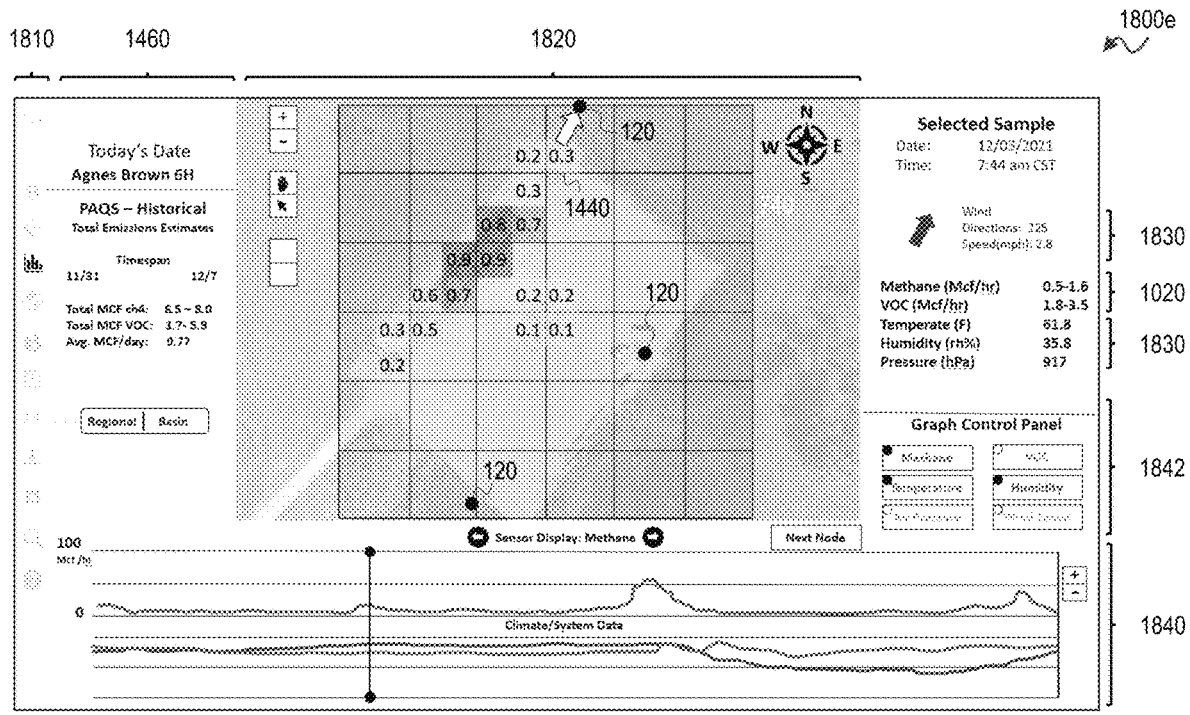
FIG. 18E is another view of the dashboard interface according to an exemplary embodiment.
Figure 18F:
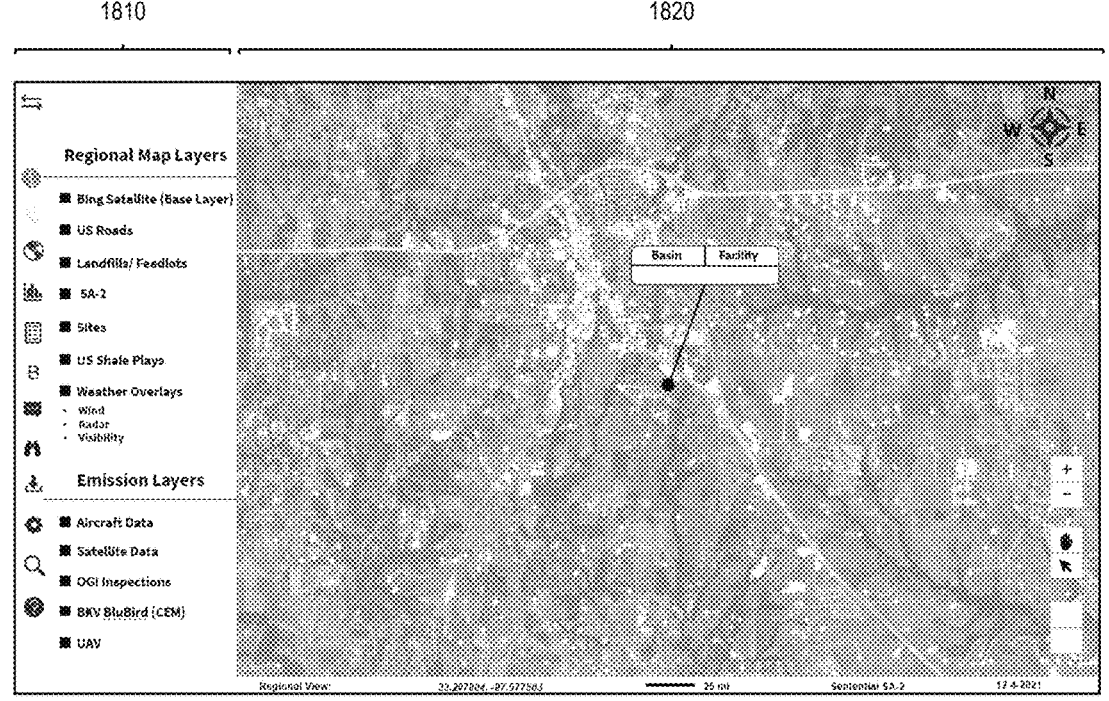
FIG. 18F is another view of the dashboard interface according to an exemplary embodiment.

FIG. 18E is a view 1800*e* of the dashboard interface 1800 according to an exemplary embodiment. In the embodiment of FIG. 18E, the color-coded grid cells 740 also include leak location probability array 1590, indicating to the user the most probable leak source at the site 10. In the absence of an alert 1790, the view 1800*e* may include the total emissions 1460 at the site 10 for default or a user-selected time period (e.g., one week, one month, the entire time period that the leak detection system 100 has been monitoring the site 10, etc.).

FIG. 18G is a regional view 1800*g* of the dashboard interface 1800 according to an exemplary embodiment. In the embodiment of FIG. 18G, the view 1800*f* includes the menu 1810 which provides functionality to view additional map layers, including imaging satellites (e.g., Sentential SA-2 and LandSAT) for the geographic area of the site 10. The regional view 1800*g* allows the user or the gas leak detection system 100 to explore off-pad events and attempt to trace them back to the source. Potential regional sources (landfills, feedlots, other well pads) can be integrated and displayed using the layers tab and, therefore, considered when off pad emissions are detected. The regional view 1800*g* also serves as a way to view imported emissions/concentration data such as aircraft, drone and some higher resolution satellite data, allowing the user to build a complete picture of the current and historical emissions profile of the site 10.

As described above, the gas leak emission and dispersion modeling process 600 combines gas concentration observations 590, wind observations 610 and 1302, and the variability of winds over time (measured at an array of sensor units 120) with a sequence of mapping and mathematical modeling steps to convert the measured gas concentrations 590 to emission rates 1440 assigned to grid cells 740 spanning the site 10 of interest. By converting those point measurements of gas concentrations 590 to spatial two- and three-dimensional maps 1820 of gas emission rates 1440 and accumulating those calculations over time and space, the gas leak detection system 100 both allows user to visualize the gas plume and identifies the most likely location of a gas leak event.

While preferred embodiments of the gas leak detection system 100 have been described above, it is important to note that none of the features described above are critical. While the sensor array 200 is described above as including metal oxide sensors 220 to measure the concentrations of natural gas (specifically, methane) and volatile organic compounds, the machine learning-enabled gas leak detection process 400 can be used to differentiate between—and measure the concentrations of—other gases using other sensors (even if, as described above, those sensors suffer from cross-sensitivities to those gases). Similarly, while the machine learning-enabled gas leak detection process 400 is described above as overcoming the sensitivity of metal oxide sensors 220 to specific humidity 446, temperature 442, relative humidity 444, and the temperature of the sensor housing, the machine learning-enabled gas leak detection process 400 can be used to compensate for sensor responsiveness to any condition (environmental or otherwise). While the features described above provide specific technical benefits when used in combination, each of those features—including the sensor units 120, the data analysis and reporting 180, the sensor suite 200, the machine learning-enabled gas leak detection process 400, the gas leak emission and dispersion modeling process 600, and the dashboard interface 1800 with two- and/or three-dimensional display visualization—may be used separately or with any combination of some or all of the aforementioned features. Therefore, while preferred embodiments of the gas leak detection system 100 have been described above, those skilled in the art who have reviewed the present disclosure will readily appreciate that other embodiments can be realized within the scope of the invention. Accordingly, the present invention should be construed as limited only by any appended claims.

What is claimed is:
1. A gas leak detection system, comprising:
  a plurality of the sensor units, deployed at a site, each sensor unit comprising:
    a sensor suite for sampling an air sample and outputting observed sensor data, the sensor suite comprising:
      one or more environmental condition sensors for measuring the temperature and humidity of the air sample; and
      an array of metal oxide sensors, each of the metal oxide sensors having different sensitivities to methane and different sensitivities to volatile organic compounds; and
    an anemometer that senses wind speed and wind direction at the site;
  non-transitory computer readable storage media that stores:
    a gas leak detection model, generated by a machine learning algorithm trained by exposing each of the metal oxide sensors to known concentrations of methane and volatile organic compounds having measured temperatures and measured humidity; and
    a gas transport model for calculating estimated gas emission rates at a plurality of locations at the site most likely to cause a measured gas concentration at each of the sensor units based on the wind speeds and wind directions at the site and surface layer air mixing conditions at the site;
  one or more processing units that:
    identify distances and bearings between each of the sensor units and each of a plurality of locations at the site;
    repeatedly receive sensor data output by each of the metal oxide sensors of each sensor unit;
    identify the temperature and humidity of each air sample;
    model relationships between the sensor data output by each metal oxide sensor and the measured temperature and humidity of each air sample;
    update the gas leak detection model based on the modeled relationships between the sensor data output by each metal oxide sensor and the measured temperature and humidity of each air sample;
    for each of the sensor units, calculate a background methane concentration based on the wind direction at the site;

use the updated gas leak detection model to generate predicted sensor data for baseline air samples having only the background methane concentrations at the temperatures and humidities of each air sample;

compare the observed sensor data output by each of the metal oxide sensors for each air sample to the predicted sensor data generated for the baseline air samples having only the background methane concentrations at the temperature and humidity of the air sample;

use the updated gas leak detection model to calculate measured methane concentrations in each air sample based on the comparisons of the sensor data output by each of the metal oxide sensors to the predicted sensor data for the baseline air sample having only the background methane concentrations;

for each of the sensor units, adjust the measured methane concentration to calculate a background-adjusted methane concentration;

estimate surface layer air mixing conditions at the site; and estimate methane emissions rates at each of the plurality of locations at the site by using the gas transport model to calculate, based on the wind speeds and wind directions at the site and the surface layer air mixing conditions at the site, the estimated methane emission rates at each of the plurality of locations most likely to cause the background-adjusted methane concentrations at each of the sensor units.

2. The system of claim 1, each sensor unit further comprising:
a sensor chamber enclosing the sensor suite;
an intake tube and an intake pump for introducing the air sample into the sensor chamber; and
an exhaust tube for evacuating the chamber,
wherein the metal oxide sensors heat the air sample inside the sensor chamber.

3. The system of claim 2, wherein:
the metal oxide sensors each include a heating plate for heating the metal oxide sensor;
the sensor suite includes a sensor housing temperature sensor that measures an external temperature of at least one of the metal oxide sensors;
the observed sensor data includes the external temperature of the at least one metal oxide sensor.

4. The system of claim 3, each sensor unit further comprising:
a heater circuit that provides a voltage to the heating plate of the at least one metal oxide sensor; and
a controller that outputs sensor control signals to the sensor heater circuit to heat and cool the at least one metal oxide sensor,
wherein the observed sensor data includes data indicative of the output of the at least one metal oxide sensor at a plurality of external temperatures.

5. The system of claim 1, wherein the array of metal oxide sensors comprises a methane-sensitive metal oxide sensor, a volatile organic compound-sensitive metal oxide sensor, and a volatile organic compound-filtered metal oxide sensor.

6. The system of claim 1, wherein the gas transport model comprises a Gaussian plume model.

7. The system of claim 1, wherein the one or more processing units identify the plurality of locations at the site by:
receiving a map or image of the site;
identifying a plurality of two- or three-dimensional grid cells at the site; and
identifying the grid cells that include a probable emissions source.

8. The system of claim 7, wherein the gas transport model calculates the estimated gas emission rate further based on the height of each air sample collected by the sensor units and the height of each of the probable emission sources.

9. The system of claim 1, wherein processing unit calculates the probability that a methane leak is occurring at each of the plurality of locations by:
estimating the methane emission rate at each of the plurality of locations using one or more measured methane concentrations output by a first sensor unit;
estimating the methane emission rate at each of the plurality of locations using one or more measured gas concentrations output by a second sensor unit; and
determining the variance, at each of the plurality of locations, between the methane emissions rates estimated using the first sensor unit and the methane emissions rates estimated using the second sensor unit.

10. The system of claim 1, further comprising a graphical user interface that outputs:
a map or image of the site;
information indicative of the estimated methane emission rate at each of the plurality of locations.

11. A gas leak detection method, comprising:
observing sensor data by a plurality of the sensor units, deployed at a site, each sensor unit including a sensor suite for sampling an air sample and outputting observed sensor data, the sensor suite comprising one or more environmental condition sensors for measuring the temperature and humidity of the air sample and an array of metal oxide sensors, each of the metal oxide sensors having different sensitivities to methane and different sensitivities to volatile organic compounds;
sensing, by an anemometer, wind speed and wind direction at the site;
storing a gas leak detection model, generated by a machine learning algorithm trained by exposing each of the metal oxide sensors to known concentrations of methane and volatile organic compounds having measured temperatures and measured humidity;
storing a gas transport model for calculating estimated gas emission rates at a plurality of locations at the site most likely to cause a measured gas concentration at each of the sensor units based on the wind speeds and wind directions at the site and surface layer air mixing conditions at the site;
identifying distances and bearings between each of the sensor units and each of a plurality of locations at the site;
repeatedly receiving sensor data output by each of the metal oxide sensors of each sensor unit;
identifying the temperature and humidity of each air sample;
modeling relationships between the sensor data output by each metal oxide sensor and the measured temperature and humidity of each air sample;
updating the gas leak detection model based on the modeled relationships between the sensor data output by each metal oxide sensor and the measured temperature and humidity of each air sample;
for each of the sensor units, calculating a background methane concentration based on the wind direction at the site;
using the updated gas leak detection model to generate predicted sensor data for air samples having only the background methane concentrations at the temperatures and humidities of each air sample;

comparing the observed sensor data output by each of the metal oxide sensors for each air sample to the predicted sensor data generated for the baseline air samples having only the background methane concentrations at the temperature and humidity of the air samples;

using the updated gas leak detection model to calculate measured methane concentrations in each air sample based on the comparisons of the sensor data output by each of the metal oxide sensors to the predicted sensor data for the baseline air sample having only the background methane concentrations;

for each of the sensor units, adjusting the measured methane concentration to calculate a background-adjusted methane concentration;

estimating surface layer air mixing conditions at the site; and estimating methane emissions rates at each of the plurality of locations at the site by using the gas transport model to calculate, based on the wind speeds and wind directions at the site and the surface layer air mixing conditions at the site, the estimated methane emission rates at each of the plurality of locations most likely to cause the background-adjusted methane concentrations at each of the sensor units.

12. The method of claim 11, each sensor unit further comprising:
a sensor chamber enclosing the sensor suite;
an intake tube and an intake pump for introducing the air sample into the sensor chamber; and
an exhaust tube for evacuating the chamber,
wherein the metal oxide sensors heat the air sample inside the sensor chamber.

13. The method of claim 12, wherein:
the metal oxide sensors each include a heating plate for heating the metal oxide sensor;
the sensor suite includes a sensor housing temperature sensor that measures an external temperature of at least one of the metal oxide sensors;
the observed sensor data includes the external temperature of the at least one metal oxide sensor.

14. The method of claim 13, each sensor unit further comprising:
a heater circuit that provides a voltage to the heating plate of the at least one metal oxide sensor; and
a controller that outputs sensor control signals to the sensor heater circuit to heat and cool the at least one metal oxide sensor,
wherein the observed sensor data includes data indicative of the output of the at least one metal oxide sensor at a plurality of external temperatures.

15. The method of claim 11, wherein the array of metal oxide sensors comprises a methane-sensitive metal oxide sensor, a volatile organic compound-sensitive metal oxide sensor, and a volatile organic compound-filtered metal oxide sensor.

16. The method of claim 11, wherein the gas transport model comprises a Gaussian plume model.

17. The method of claim 11, wherein the plurality of locations at the site are identified by:
receiving a map or image of the site;
identifying a plurality of two- or three-dimensional grid cells at the site; and
identifying the grid cells that include a probable emissions source.

18. The method of claim 17, wherein the gas transport model calculates the estimated gas emission rate further based on the height of each air sample collected by the sensor units and the height of each of the probable emission sources.

19. The method of claim 11, further comprising:
calculating the probability that a methane leak is occurring at each of the plurality of locations by:
estimating the methane emission rate at each of the plurality of locations using one or more measured methane concentrations output by a first sensor unit;
estimating the methane emission rate at each of the plurality of locations using one or more measured gas concentrations output by a second sensor unit; and
determining the variance, at each of the plurality of locations, between the methane emissions rates estimated using the first sensor unit and the methane emissions rates estimated using the second sensor unit.

20. The method of claim 11, further comprising:
outputting, via a graphical user interface, a map or image of the site;
outputting, via the graphical user interface, information indicative of the estimated methane emission rate at each of the plurality of locations.

* * * * *